(12) United States Patent
Stone

(10) Patent No.: US 7,601,165 B2
(45) Date of Patent: Oct. 13, 2009

(54) METHOD AND APPARATUS FOR FORMING A SELF-LOCKING ADJUSTABLE SUTURE LOOP

(75) Inventor: Kevin T Stone, Winona Lake, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 444 days.

(21) Appl. No.: 11/541,506

(22) Filed: Sep. 29, 2006

(65) Prior Publication Data

US 2008/0082128 A1   Apr. 3, 2008

(51) Int. Cl.
*A61B 17/04* (2006.01)

(52) U.S. Cl. ...................................... 606/232

(58) Field of Classification Search ............... 606/232, 606/223–225, 228, 74, 103; 52/22; 604/103.04; 24/115 H
See application file for complete search history.

(56) References Cited

U.S. PATENT DOCUMENTS

| 26,501 | A | 12/1859 | Kendrick et al. |
| 64,499 | A | 6/1867 | Miller |
| 65,499 | A | 6/1867 | Miller |
| 126,366 | A | 4/1872 | Wills |
| 233,475 | A | 10/1880 | Cook et al. |
| 261,501 | A | 7/1882 | Vandermark |
| 417,805 | A | 12/1889 | Beaman |
| 487,304 | A | 12/1892 | Todd |
| 762,710 | A | 6/1904 | Hall |
| 837,767 | A | 12/1906 | Aims |
| 838,203 | A | 12/1906 | Neil |
| 1,059,631 | A | 4/1913 | Popovics |
| 1,131,155 | A | 3/1915 | Murphy |
| 1,153,450 | A | 9/1915 | Schaff |
| 1,346,940 | A | 7/1920 | Collins |
| 1,635,066 | A | 7/1927 | Wells |
| 1,950,799 | A | 3/1934 | Jones |
| 2,065,659 | A | 12/1936 | Cullen |
| 2,108,206 | A | 2/1938 | Meeker |
| 2,121,193 | A | 6/1938 | Hanicke |
| 2,242,003 | A | 5/1941 | Lorenzo |
| 2,267,925 | A | 12/1941 | Johnston |

(Continued)

FOREIGN PATENT DOCUMENTS

| AU | 4957264 | 3/1966 |
| AU | 440266 | 10/1967 |
| AU | 2223767 | 11/1968 |
| AU | 5028569 | 8/1970 |
| AU | 5850469 | 1/1971 |

(Continued)

OTHER PUBLICATIONS

"EZ Loc Femoral Fixation Device," copyright 2005 Arthrotek, Inc. 8 sheets.

(Continued)

*Primary Examiner*—(Jackie) Tan-Uyen T Ho
*Assistant Examiner*—Son Dang
(74) *Attorney, Agent, or Firm*—Harness, Dickey

(57) ABSTRACT

A method and apparatus for coupling a soft tissue implant into a locking cavity formed within a bone is disclosed. The apparatus includes a member to pull the soft tissue implant into a femoral tunnel. The member includes a suture having first and second ends which are passed through first and second openings associated with the longitudinal passage to form a pair of loops. Portions of the suture lay parallel to each other within the suture. Application of tension onto the suture construction causes retraction of the soft tissue implant into the femoral tunnel.

21 Claims, 11 Drawing Sheets

U.S. PATENT DOCUMENTS

| | | |
|---|---|---|
| 2,302,986 A | 11/1942 | Vollrath |
| 2,329,398 A | 9/1943 | Duffy |
| RE22,857 E | 3/1947 | Ogburn |
| 2,526,959 A | 10/1950 | Lorenzo |
| 2,528,456 A | 10/1950 | Stevenson |
| 2,562,419 A | 7/1951 | Ferris |
| 2,581,564 A | 1/1952 | Villegas |
| 2,600,395 A | 1/1952 | Domoj et al. |
| 2,665,597 A | 1/1954 | Hill |
| 2,669,774 A | 2/1954 | Mitchell |
| 2,698,986 A | 1/1955 | Brown |
| 2,760,488 A | 8/1956 | Pierce |
| 2,833,284 A | 5/1958 | Springer |
| 2,846,712 A | 8/1958 | Markman |
| 2,860,393 A | 11/1958 | Brock |
| 2,880,728 A | 4/1959 | Rights |
| 2,881,762 A | 4/1959 | Lowrie |
| 2,883,096 A | 4/1959 | Dawson |
| 2,913,042 A | 11/1959 | Taylor |
| 3,000,009 A | 9/1961 | Selstad |
| 3,003,155 A | 10/1961 | Mielzynski et al. |
| 3,013,559 A | 12/1961 | Thomas |
| 3,037,619 A | 6/1962 | Stevans |
| 3,039,460 A | 6/1962 | Chandler |
| 3,090,386 A | 5/1963 | Curtis |
| 3,103,666 A | 9/1963 | Bone |
| 3,123,077 A | 3/1964 | Alcamo |
| 3,125,095 A | 3/1964 | Kaufman et al. |
| 3,209,422 A | 10/1965 | Dritz |
| 3,234,938 A | 2/1966 | Robinson |
| 3,240,379 A | 3/1966 | Bremer et al. |
| 3,250,271 A | 5/1966 | Lippes |
| 3,399,432 A | 9/1968 | Merser |
| 3,409,014 A | 11/1968 | Shannon |
| 3,435,475 A | 4/1969 | Bisk |
| 3,467,089 A | 9/1969 | Hasson |
| 3,470,834 A | 10/1969 | Bone |
| 3,470,875 A | 10/1969 | Johnson |
| 3,500,820 A | 3/1970 | Almen |
| 3,507,274 A | 4/1970 | Soichet |
| 3,513,484 A | 5/1970 | Hausner |
| 3,515,132 A | 6/1970 | McKnight |
| 3,522,803 A | 8/1970 | Majzlin |
| 3,527,223 A | 9/1970 | Shein |
| 3,533,406 A | 10/1970 | Hutterer et al. |
| 3,541,591 A | 11/1970 | Hoegerman |
| 3,547,389 A | 12/1970 | Mitchell |
| 3,579,831 A | 5/1971 | Stevens et al. |
| 3,590,616 A | 7/1971 | Schussler et al. |
| 3,618,447 A | 11/1971 | Coins |
| 3,628,530 A | 12/1971 | Schwartz |
| 3,643,649 A | 2/1972 | Amato |
| 3,648,705 A | 3/1972 | Lary |
| 3,656,483 A | 4/1972 | Rudel |
| 3,664,345 A | 5/1972 | Dabbs et al. |
| 3,665,560 A | 5/1972 | Bennett et al. |
| 3,675,639 A | 7/1972 | Cimber |
| 3,683,422 A | 8/1972 | Stemmer et al. |
| 3,692,022 A | 9/1972 | Ewing |
| 3,695,271 A | 10/1972 | Chodorow |
| 3,699,969 A | 10/1972 | Allen |
| 3,716,058 A | 2/1973 | Tanner, Jr. |
| 3,744,488 A | 7/1973 | Cox |
| 3,752,516 A | 8/1973 | Mumma |
| 3,757,629 A | 9/1973 | Schneider |
| 3,763,856 A | 10/1973 | Blomberg |
| 3,771,520 A | 11/1973 | Lerner |
| 3,777,748 A | 12/1973 | Abramson |
| 3,807,407 A | 4/1974 | Schweizer |
| 3,825,010 A | 7/1974 | McDonald |
| 3,840,017 A | 10/1974 | Violante et al. |
| 3,842,824 A | 10/1974 | Neufeld |
| 3,842,840 A | 10/1974 | Schweizer |
| 3,845,772 A | 11/1974 | Smith |
| 3,867,933 A | 2/1975 | Kitrilakis |
| 3,867,944 A | 2/1975 | Samuels |
| 3,871,368 A | 3/1975 | Johnson et al. |
| 3,871,379 A | 3/1975 | Clarke |
| 3,874,388 A | 4/1975 | King et al. |
| 3,875,648 A | 4/1975 | Bone |
| 3,877,570 A | 4/1975 | Barry |
| 3,880,156 A | 4/1975 | Hoff |
| 3,881,475 A | 5/1975 | Gordon et al. |
| 3,889,666 A | 6/1975 | Lerner |
| 3,892,240 A | 7/1975 | Park |
| 3,896,500 A | 7/1975 | Rambert et al. |
| 3,907,442 A | 9/1975 | Reid |
| 3,910,281 A | 10/1975 | Kletschka et al. |
| 3,918,444 A | 11/1975 | Hoff et al. |
| 3,927,666 A | 12/1975 | Hoff |
| 3,931,667 A | 1/1976 | Merser et al. |
| 3,933,153 A | 1/1976 | Csatary et al. |
| 3,937,217 A | 2/1976 | Kosonen |
| 3,943,932 A | 3/1976 | Woo |
| 3,946,728 A | 3/1976 | Bettex |
| 3,946,740 A | 3/1976 | Bassett |
| 3,953,896 A | 5/1976 | Treace |
| 3,954,103 A | 5/1976 | Garcia-Roel et al. |
| 3,961,632 A | 6/1976 | Moossun |
| 3,973,560 A | 8/1976 | Emmett |
| 3,976,079 A | 8/1976 | Samuels et al. |
| 3,977,050 A | 8/1976 | Perez |
| 3,979,799 A | 9/1976 | Merser et al. |
| 3,985,138 A | 10/1976 | Jarvik |
| 3,990,619 A | 11/1976 | Russell |
| 4,005,707 A | 2/1977 | Moulding, Jr. |
| 4,006,747 A | 2/1977 | Kronenthal et al. |
| 4,007,743 A | 2/1977 | Blake |
| 4,013,071 A | 3/1977 | Rosenberg |
| 4,026,281 A | 5/1977 | Mayberry et al. |
| 4,050,100 A | 9/1977 | Barry |
| 4,054,954 A | 10/1977 | Nakayama et al. |
| 4,085,466 A | 4/1978 | Goodfellow et al. |
| 4,094,313 A | 6/1978 | Komamura et al. |
| 4,103,690 A | 8/1978 | Harris |
| RE29,819 E | 10/1978 | Bone |
| 4,121,487 A | 10/1978 | Bone |
| 4,143,656 A | 3/1979 | Holmes et al. |
| 4,144,876 A | 3/1979 | DeLeo |
| 4,149,277 A | 4/1979 | Bokros |
| 4,157,714 A | 6/1979 | Foltz et al. |
| 4,160,453 A | 7/1979 | Miller |
| 4,164,225 A | 8/1979 | Johnson et al. |
| 4,172,458 A | 10/1979 | Pereyra |
| 4,175,555 A | 11/1979 | Herbert et al. |
| 4,185,636 A | 1/1980 | Gabbay et al. |
| 4,196,883 A | 4/1980 | Einhorn et al. |
| 4,210,148 A | 7/1980 | Stivala |
| 4,235,161 A | 11/1980 | Kunreuther |
| 4,235,238 A | 11/1980 | Ogiu et al. |
| 4,237,779 A | 12/1980 | Kunreuther |
| 4,243,037 A | 1/1981 | Smith |
| 4,249,525 A | 2/1981 | Krzeminski |
| 4,263,913 A | 4/1981 | Malmin |
| 4,265,246 A | 5/1981 | Barry |
| 4,273,117 A | 6/1981 | Neuhauser |
| 4,275,717 A | 6/1981 | Bolesky |
| 4,287,807 A | 9/1981 | Pacharis et al. |
| 4,291,698 A | 9/1981 | Fuchs et al. |
| 4,301,551 A | 11/1981 | Dore et al. |
| 4,312,337 A | 1/1982 | Donohue |
| 4,316,469 A | 2/1982 | Kapitanov et al. |
| 4,326,531 A | 4/1982 | Shimonaka |
| 4,345,601 A | 8/1982 | Fukuda |

| | | |
|---|---|---|
| 4,349,027 A | 9/1982 | DiFrancesco |
| 4,388,921 A | 6/1983 | Sutter et al. |
| 4,400,833 A | 8/1983 | Kurland |
| 4,402,445 A | 9/1983 | Green |
| 4,409,974 A | 10/1983 | Freedland |
| 4,438,769 A | 3/1984 | Pratt et al. |
| 4,441,489 A | 4/1984 | Evans et al. |
| 4,454,875 A | 6/1984 | Pratt et al. |
| 4,462,395 A | 7/1984 | Johnson |
| 4,463,753 A | 8/1984 | Gustilo |
| 4,473,102 A | 9/1984 | Ohman et al. |
| 4,484,570 A | 11/1984 | Sutter et al. |
| 4,493,323 A | 1/1985 | Albright et al. |
| 4,496,468 A | 1/1985 | House et al. |
| 4,505,274 A | 3/1985 | Speelman |
| 4,509,516 A | 4/1985 | Richmond |
| 4,531,522 A | 7/1985 | Bedi et al. |
| 4,532,926 A | 8/1985 | O'Holla |
| 4,534,350 A | 8/1985 | Golden et al. |
| 4,535,764 A | 8/1985 | Ebert |
| 4,537,185 A | 8/1985 | Stednitz |
| 4,549,545 A * | 10/1985 | Levy .................... 606/228 |
| 4,549,652 A | 10/1985 | Free |
| 4,561,432 A | 12/1985 | Mazor |
| 4,564,007 A | 1/1986 | Coombs et al. |
| 4,570,623 A | 2/1986 | Ellison et al. |
| 4,573,844 A | 3/1986 | Smith |
| 4,576,608 A | 3/1986 | Homsy |
| 4,584,722 A | 4/1986 | Levy et al. |
| 4,590,928 A | 5/1986 | Hunt et al. |
| 4,595,007 A | 6/1986 | Mericle |
| 4,596,249 A | 6/1986 | Freda et al. |
| 4,602,635 A | 7/1986 | Mulhollan et al. |
| 4,602,636 A | 7/1986 | Noiles |
| 4,604,997 A | 8/1986 | De Bastiani et al. |
| 4,605,414 A | 8/1986 | Czajka |
| 4,616,650 A | 10/1986 | Green et al. |
| 4,621,640 A | 11/1986 | Mulhollan et al. |
| 4,624,254 A | 11/1986 | McGarry et al. |
| 4,632,100 A | 12/1986 | Somers et al. |
| 4,635,637 A | 1/1987 | Schreiber |
| 4,636,121 A | 1/1987 | Miller |
| 4,641,652 A | 2/1987 | Hutterer et al. |
| 4,649,952 A | 3/1987 | Jobe |
| 4,653,486 A | 3/1987 | Coker |
| 4,653,487 A | 3/1987 | Maale |
| 4,653,489 A | 3/1987 | Tronzo |
| 4,655,777 A | 4/1987 | Dunn et al. |
| 4,662,068 A | 5/1987 | Polonsky |
| 4,667,662 A | 5/1987 | Titone et al. |
| 4,667,675 A | 5/1987 | Davis |
| 4,669,473 A | 6/1987 | Richards et al. |
| 4,683,895 A | 8/1987 | Pohndorf |
| 4,688,561 A | 8/1987 | Reese |
| 4,690,169 A | 9/1987 | Jobe |
| 4,705,040 A | 11/1987 | Mueller et al. |
| 4,708,132 A | 11/1987 | Silvestrini |
| 4,716,893 A | 1/1988 | Fischer et al. |
| 4,719,671 A | 1/1988 | Ito et al. |
| 4,719,917 A | 1/1988 | Barrows et al. |
| 4,723,540 A | 2/1988 | Gilmer, Jr. |
| 4,724,839 A | 2/1988 | Bedi et al. |
| 4,728,332 A | 3/1988 | Albrektsson |
| 4,738,255 A | 4/1988 | Goble et al. |
| 4,741,330 A | 5/1988 | Hayhurst |
| 4,741,336 A | 5/1988 | Failla et al. |
| 4,744,353 A | 5/1988 | McFarland |
| 4,744,793 A | 5/1988 | Parr et al. |
| 4,750,492 A | 6/1988 | Jacobs |
| 4,760,843 A | 8/1988 | Fischer et al. |
| 4,760,848 A | 8/1988 | Hasson |
| 4,772,261 A | 9/1988 | Von Hoff et al. |
| 4,772,286 A | 9/1988 | Goble et al. |
| 4,773,910 A | 9/1988 | Chen et al. |
| 4,775,380 A | 10/1988 | Seedhom et al. |
| 4,776,328 A | 10/1988 | Frey et al. |
| 4,781,190 A | 11/1988 | Lee et al. |
| 4,784,126 A | 11/1988 | Hourahane et al. |
| 4,787,882 A | 11/1988 | Claren et al. |
| 4,790,297 A | 12/1988 | Luque et al. |
| 4,809,695 A | 3/1989 | Gwathmey et al. |
| 4,813,406 A | 3/1989 | Ogle, II |
| 4,823,794 A | 4/1989 | Pierce |
| 4,828,562 A | 5/1989 | Kenna |
| 4,832,026 A | 5/1989 | Jones |
| 4,834,098 A | 5/1989 | Jones |
| 4,841,960 A | 6/1989 | Garner |
| 4,851,005 A | 7/1989 | Hunt et al. |
| 4,858,608 A | 8/1989 | McQuilkin et al. |
| 4,860,513 A | 8/1989 | Whitman |
| 4,863,383 A | 9/1989 | Grafelmann |
| 4,870,957 A | 10/1989 | Goble et al. |
| 4,873,976 A | 10/1989 | Schreiber |
| 4,887,601 A | 12/1989 | Richards |
| 4,890,615 A | 1/1990 | Caspari et al. |
| 4,893,619 A | 1/1990 | Dale et al. |
| 4,893,974 A | 1/1990 | Fischer et al. |
| 4,895,148 A | 1/1990 | Bays et al. |
| 4,896,668 A | 1/1990 | Popoff et al. |
| 4,898,156 A | 2/1990 | Gatturna et al. |
| 4,899,743 A | 2/1990 | Nicholson et al. |
| 4,901,721 A | 2/1990 | Hakki |
| 4,923,461 A | 5/1990 | Caspari et al. |
| 4,927,421 A | 5/1990 | Goble et al. |
| 4,946,468 A | 8/1990 | Li |
| 4,950,270 A | 8/1990 | Bowman et al. |
| 4,950,285 A * | 8/1990 | Wilk .................... 606/232 |
| 4,960,381 A | 10/1990 | Niznick |
| 4,961,741 A | 10/1990 | Hayhurst |
| 4,968,315 A | 11/1990 | Gatturna |
| 4,968,317 A | 11/1990 | Tormala et al. |
| 4,969,886 A | 11/1990 | Cziffer et al. |
| 4,976,736 A | 12/1990 | White et al. |
| 4,978,350 A | 12/1990 | Wagenknecht et al. |
| 4,979,956 A | 12/1990 | Silvestrini |
| 4,983,176 A | 1/1991 | Cushman et al. |
| 4,988,351 A | 1/1991 | Paulos et al. |
| 4,997,433 A | 3/1991 | Goble et al. |
| 5,002,550 A | 3/1991 | Li |
| 5,002,562 A | 3/1991 | Oberlander |
| 5,007,921 A | 4/1991 | Brown |
| 5,030,224 A | 7/1991 | Wright et al. |
| 5,037,422 A | 8/1991 | Hayhurst et al. |
| 5,041,129 A | 8/1991 | Hayhurst et al. |
| 5,046,513 A | 9/1991 | Gatturna et al. |
| 5,047,030 A | 9/1991 | Draenert et al. |
| 5,053,046 A | 10/1991 | Janese |
| 5,053,047 A | 10/1991 | Yoon |
| 5,059,201 A | 10/1991 | Asnis |
| 5,059,206 A | 10/1991 | Winters |
| 5,062,344 A * | 11/1991 | Gerker .................... 87/8 |
| 5,062,843 A | 11/1991 | Mahony |
| 5,078,731 A | 1/1992 | Hayhurst |
| 5,078,843 A | 1/1992 | Pratt |
| 5,084,050 A | 1/1992 | Draenert |
| 5,084,058 A | 1/1992 | Li |
| 5,085,661 A | 2/1992 | Moss |
| 5,087,263 A | 2/1992 | Li |
| 5,092,866 A | 3/1992 | Breard et al. |
| 5,098,435 A | 3/1992 | Stednitz et al. |
| 5,100,415 A | 3/1992 | Hayhurst |
| 5,100,417 A | 3/1992 | Cerier et al. |
| 5,116,337 A | 5/1992 | Johnson |
| 5,116,373 A | 5/1992 | Jakob et al. |
| 5,116,375 A | 5/1992 | Hofmann |
| 5,123,913 A | 6/1992 | Wilk et al. |

| | | | | | | |
|---|---|---|---|---|---|---|
| 5,127,785 A | 7/1992 | Faucher et al. | | 5,368,599 A | 11/1994 | Hirsch et al. |
| 5,129,901 A | 7/1992 | Decoste | | 5,370,661 A | 12/1994 | Branch |
| 5,129,902 A | 7/1992 | Goble et al. | | 5,370,662 A | 12/1994 | Stone et al. |
| 5,129,904 A | 7/1992 | Illi et al. | | 5,372,146 A | 12/1994 | Branch |
| 5,129,906 A | 7/1992 | Ross et al. | | 5,372,604 A | 12/1994 | Trott |
| 5,139,499 A | 8/1992 | Small et al. | | 5,372,821 A | 12/1994 | Badylak et al. |
| 5,139,520 A | 8/1992 | Rosenberg | | 5,374,268 A | 12/1994 | Sander |
| 5,143,498 A | 9/1992 | Whitman | | 5,379,492 A | 1/1995 | Glesser |
| 5,147,362 A | 9/1992 | Goble | | 5,383,878 A | 1/1995 | Roger et al. |
| 5,149,329 A | 9/1992 | Richardson | | 5,383,904 A * | 1/1995 | Totakura et al. ............. 606/228 |
| 5,152,790 A | 10/1992 | Rosenberg et al. | | 5,391,171 A | 2/1995 | Schmieding |
| 5,154,189 A | 10/1992 | Oberlander | | 5,391,176 A | 2/1995 | de la Torre |
| 5,156,616 A | 10/1992 | Meadows et al. | | 5,393,302 A | 2/1995 | Clark et al. |
| 5,163,960 A | 11/1992 | Bonutti | | RE34,871 E | 3/1995 | McGuire et al. |
| D331,626 S | 12/1992 | Hayhurst et al. | | 5,397,356 A | 3/1995 | Goble et al. |
| 5,169,400 A | 12/1992 | Muhling et al. | | 5,403,328 A | 4/1995 | Shallman |
| 5,176,682 A | 1/1993 | Chow | | 5,403,329 A | 4/1995 | Hinchcliffe |
| 5,178,629 A | 1/1993 | Kammerer | | 5,403,348 A | 4/1995 | Bonutti |
| 5,183,458 A | 2/1993 | Marx | | 5,417,691 A | 5/1995 | Hayhurst |
| 5,192,282 A | 3/1993 | Draenert et al. | | 5,417,712 A | 5/1995 | Whittaker et al. |
| 5,197,987 A | 3/1993 | Koch et al. | | 5,423,819 A | 6/1995 | Small et al. |
| 5,203,784 A | 4/1993 | Ross et al. | | 5,423,823 A | 6/1995 | Schmieding |
| 5,203,787 A | 4/1993 | Noblitt et al. | | 5,423,860 A | 6/1995 | Lizardi et al. |
| 5,207,679 A | 5/1993 | Li | | 5,425,733 A | 6/1995 | Schmieding |
| 5,209,753 A | 5/1993 | Biedermann et al. | | 5,425,766 A | 6/1995 | Bowald et al. |
| 5,209,805 A | 5/1993 | Spraggins | | 5,433,751 A | 7/1995 | Christel et al. |
| 5,211,647 A | 5/1993 | Schmieding | | 5,437,680 A | 8/1995 | Yoon |
| 5,211,650 A | 5/1993 | Noda | | 5,439,684 A | 8/1995 | Prewett et al. |
| 5,214,987 A | 6/1993 | Fenton, Sr. | | 5,443,468 A | 8/1995 | Johnson |
| 5,219,359 A | 6/1993 | McQuilkin et al. | | 5,443,482 A | 8/1995 | Stone et al. |
| 5,224,946 A | 7/1993 | Hayhurst et al. | | 5,443,483 A | 8/1995 | Kirsch et al. |
| 5,230,699 A | 7/1993 | Grasinger | | 5,443,509 A | 8/1995 | Boucher et al. |
| 5,232,436 A | 8/1993 | Janevski | | 5,445,833 A | 8/1995 | Badylak et al. |
| 5,234,435 A | 8/1993 | Seagrave, Jr. | | 5,447,512 A | 9/1995 | Wilson et al. |
| 5,235,238 A | 8/1993 | Nomura et al. | | 5,451,203 A | 9/1995 | Lamb |
| 5,236,445 A | 8/1993 | Hayhurst et al. | | 5,454,811 A | 10/1995 | Huebner |
| 5,236,461 A | 8/1993 | Forte | | 5,456,685 A | 10/1995 | Huebner |
| 5,242,447 A | 9/1993 | Borzone | | 5,456,722 A | 10/1995 | McLeod et al. |
| 5,246,441 A | 9/1993 | Ross | | 5,458,601 A | 10/1995 | Young, Jr. et al. |
| 5,249,899 A | 10/1993 | Wilson | | 5,458,604 A | 10/1995 | Schmieding |
| 5,258,015 A | 11/1993 | Li et al. | | 5,462,560 A | 10/1995 | Stevens |
| 5,258,016 A | 11/1993 | DiPoto et al. | | 5,464,426 A | 11/1995 | Bonutti |
| 5,258,040 A * | 11/1993 | Bruchman et al. ............. 57/21 | | 5,464,427 A | 11/1995 | Curtis et al. |
| 5,268,001 A | 12/1993 | Nicholson et al. | | 5,464,440 A | 11/1995 | Johansson |
| 5,269,160 A | 12/1993 | Wood | | 5,466,237 A | 11/1995 | Byrd, III et al. |
| 5,269,783 A | 12/1993 | Sander | | 5,467,786 A | 11/1995 | Allen et al. |
| 5,269,809 A | 12/1993 | Hayhurst et al. | | 5,470,334 A | 11/1995 | Ross et al. |
| 5,281,422 A | 1/1994 | Badylak et al. | | 5,470,337 A | 11/1995 | Moss |
| 5,282,809 A | 2/1994 | Zammerer et al. | | 5,470,338 A | 11/1995 | Whitfield et al. |
| 5,282,832 A | 2/1994 | Toso et al. | | 5,472,452 A | 12/1995 | Trott |
| 5,285,040 A | 2/1994 | Brandberg et al. | | 5,474,565 A | 12/1995 | Trott |
| 5,290,217 A | 3/1994 | Campos | | 5,474,568 A | 12/1995 | Scott |
| 5,306,301 A | 4/1994 | Graf et al. | | 5,474,572 A | 12/1995 | Hayhurst |
| 5,312,422 A | 5/1994 | Trott | | 5,478,344 A | 12/1995 | Stone et al. |
| 5,312,438 A | 5/1994 | Johnson | | 5,478,345 A | 12/1995 | Stone et al. |
| 5,318,577 A | 6/1994 | Li | | 5,480,403 A | 1/1996 | Lee et al. |
| 5,318,578 A | 6/1994 | Hasson | | 5,480,406 A | 1/1996 | Nolan et al. |
| 5,320,115 A | 6/1994 | Kenna | | 5,484,442 A | 1/1996 | Melker et al. |
| 5,320,626 A | 6/1994 | Schmieding | | 5,486,197 A | 1/1996 | Le et al. |
| 5,320,633 A | 6/1994 | Allen et al. | | 5,490,750 A | 2/1996 | Gundy |
| 5,324,308 A | 6/1994 | Pierce | | 5,496,331 A | 3/1996 | Xu et al. |
| 5,334,204 A | 8/1994 | Clewett et al. | | 5,496,348 A | 3/1996 | Bonutti |
| 5,336,229 A | 8/1994 | Noda | | 5,500,000 A | 3/1996 | Feagin et al. |
| 5,336,231 A | 8/1994 | Adair | | 5,505,736 A | 4/1996 | Reimels et al. |
| 5,336,240 A | 8/1994 | Metzler et al. | | 5,507,754 A | 4/1996 | Green et al. |
| 5,342,369 A | 8/1994 | Harryman, II | | 5,520,691 A | 5/1996 | Branch |
| 5,346,462 A | 9/1994 | Barber | | 5,520,702 A | 5/1996 | Sauer et al. |
| 5,354,298 A | 10/1994 | Lee et al. | | 5,522,817 A | 6/1996 | Sander et al. |
| 5,356,413 A | 10/1994 | Martins et al. | | 5,522,820 A | 6/1996 | Caspari et al. |
| 5,358,511 A | 10/1994 | Gatturna et al. | | 5,522,844 A | 6/1996 | Johnson |
| 5,360,431 A | 11/1994 | Puno et al. | | 5,522,845 A | 6/1996 | Wenstrom, Jr. |
| 5,362,294 A | 11/1994 | Seitzinger | | 5,522,846 A | 6/1996 | Bonutti |
| 5,364,400 A | 11/1994 | Rego, Jr. et al. | | 5,524,946 A | 6/1996 | Thompson |

| | | | | | | |
|---|---|---|---|---|---|---|
| 5,527,321 | A | 6/1996 | Hinchliffe | 5,702,462 A | 12/1997 | Oberlander |
| 5,527,342 | A | 6/1996 | Pietrzak et al. | 5,707,373 A | 1/1998 | Sevrain et al. |
| 5,527,343 | A | 6/1996 | Bonutti | 5,713,005 A | 1/1998 | Proebsting |
| 5,534,012 | A | 7/1996 | Bonutti | 5,713,904 A | 2/1998 | Errico et al. |
| 5,540,718 | A | 7/1996 | Bartlett | 5,713,905 A | 2/1998 | Goble et al. |
| 5,545,178 | A | 8/1996 | Kensey et al. | 5,713,921 A | 2/1998 | Bonutti |
| 5,545,228 | A | 8/1996 | Kambin | 5,716,359 A | 2/1998 | Ojima et al. |
| 5,549,613 | A | 8/1996 | Goble et al. | 5,718,717 A | 2/1998 | Bonutti |
| 5,549,617 | A | 8/1996 | Green et al. | 5,720,747 A * | 2/1998 | Burke ......................... 606/74 |
| 5,549,630 | A | 8/1996 | Bonutti | 5,720,765 A | 2/1998 | Thal |
| 5,549,631 | A | 8/1996 | Bonutti | 5,720,766 A | 2/1998 | Zang et al. |
| 5,562,683 | A | 10/1996 | Chan | 5,725,549 A | 3/1998 | Lam |
| 5,562,685 | A | 10/1996 | Mollenauer et al. | 5,725,556 A | 3/1998 | Moser et al. |
| 5,562,686 | A | 10/1996 | Sauer et al. | 5,725,581 A | 3/1998 | Brånemark et al. |
| 5,569,305 | A | 10/1996 | Bonutti | 5,725,582 A * | 3/1998 | Bevan et al. ................. 606/263 |
| 5,571,090 | A | 11/1996 | Sherts | 5,726,722 A | 3/1998 | Uehara et al. |
| 5,571,139 | A | 11/1996 | Jenkins, Jr. | 5,728,107 A | 3/1998 | Zlock et al. |
| 5,572,655 | A | 11/1996 | Tuljapurkar et al. | 5,728,109 A | 3/1998 | Schulze et al. |
| 5,573,286 | A | 11/1996 | Rogozinski | 5,728,136 A | 3/1998 | Thal |
| 5,573,548 | A | 11/1996 | Nazre et al. | 5,733,293 A | 3/1998 | Scirica et al. |
| 5,578,057 | A | 11/1996 | Wenstrom, Jr. | 5,733,306 A | 3/1998 | Bonutti |
| 5,584,695 | A | 12/1996 | Lal Sachdeva et al. | 5,733,307 A | 3/1998 | Dinsdale |
| 5,584,835 | A | 12/1996 | Greenfield | 5,735,875 A | 4/1998 | Bonutti et al. |
| 5,584,836 | A | 12/1996 | Ballintyn et al. | 5,741,259 A | 4/1998 | Chan |
| 5,584,862 | A | 12/1996 | Bonutti | 5,741,281 A | 4/1998 | Martin et al. |
| 5,586,986 | A | 12/1996 | Hinchliffe | 5,743,912 A | 4/1998 | Lahille et al. |
| 5,588,575 | A | 12/1996 | Davignon | 5,746,751 A | 5/1998 | Sherts |
| 5,591,180 | A | 1/1997 | Hinchliffe | 5,746,752 A | 5/1998 | Burkhart |
| 5,591,181 | A | 1/1997 | Stone et al. | 5,746,754 A | 5/1998 | Chan |
| 5,591,207 | A | 1/1997 | Coleman | 5,749,898 A | 5/1998 | Schulze et al. |
| 5,593,407 | A | 1/1997 | Reis et al. | 5,755,729 A | 5/1998 | de la Torre et al. |
| 5,593,425 | A | 1/1997 | Bonutti et al. | 5,766,176 A | 6/1998 | Duncan |
| 5,601,557 | A | 2/1997 | Hayhurst | 5,766,250 A | 6/1998 | Chervitz et al. |
| 5,601,559 | A | 2/1997 | Melker et al. | 5,769,894 A | 6/1998 | Ferragamo |
| 5,601,571 | A | 2/1997 | Moss | 5,769,899 A | 6/1998 | Schwartz et al. |
| 5,603,716 | A | 2/1997 | Morgan et al. | 5,772,673 A | 6/1998 | Cuny et al. |
| 5,607,429 | A | 3/1997 | Hayano et al. | 5,776,196 A | 7/1998 | Matsuzaki et al. |
| 5,618,290 | A | 4/1997 | Toy et al. | 5,782,862 A | 7/1998 | Bonutti |
| 5,628,756 | A * | 5/1997 | Barker et al. ................. 606/139 | 5,782,864 A | 7/1998 | Lizardi |
| 5,628,766 | A | 5/1997 | Johnson | 5,782,866 A | 7/1998 | Wenstrom, Jr. |
| 5,630,824 | A | 5/1997 | Hart | 5,785,714 A | 7/1998 | Morgan et al. |
| 5,632,748 | A | 5/1997 | Beck, Jr. et al. | 5,792,142 A | 8/1998 | Galitzer |
| 5,641,256 | A | 6/1997 | Gundy | 5,792,149 A | 8/1998 | Sherts et al. |
| 5,643,266 | A | 7/1997 | Li | 5,796,127 A | 8/1998 | Hayafuji et al. |
| 5,643,269 | A | 7/1997 | Harle et al. | 5,797,928 A | 8/1998 | Kogasaka et al. |
| 5,643,320 | A | 7/1997 | Lower et al. | 5,800,407 A | 9/1998 | Eldor et al. |
| 5,643,321 | A | 7/1997 | McDevitt | 5,810,824 A | 9/1998 | Chan |
| 5,645,546 | A | 7/1997 | Fard | 5,810,848 A | 9/1998 | Hayhurst |
| 5,645,547 | A | 7/1997 | Coleman | 5,814,069 A | 9/1998 | Schulze et al. |
| 5,645,568 | A * | 7/1997 | Chervitz et al. ............. 606/228 | 5,814,070 A | 9/1998 | Borzone et al. |
| 5,645,588 | A | 7/1997 | Graf et al. | 5,814,072 A | 9/1998 | Bonutti |
| 5,647,874 | A | 7/1997 | Hayhurst | 5,814,073 A | 9/1998 | Bonutti |
| 5,649,963 | A | 7/1997 | McDevitt | 5,823,980 A | 10/1998 | Kopfer |
| 5,658,289 | A | 8/1997 | Boucher et al. | 5,824,011 A | 10/1998 | Stone et al. |
| 5,658,299 | A | 8/1997 | Hart | 5,843,084 A | 12/1998 | Hart et al. |
| 5,658,313 | A | 8/1997 | Thal | 5,845,645 A | 12/1998 | Bonutti |
| 5,662,658 | A | 9/1997 | Wenstrom, Jr. | 5,846,254 A | 12/1998 | Schulze et al. |
| 5,662,663 | A | 9/1997 | Shallman | 5,848,983 A | 12/1998 | Basaj et al. |
| 5,665,112 | A | 9/1997 | Thal | 5,860,973 A | 1/1999 | Michelson |
| 5,667,513 | A | 9/1997 | Torrie et al. | 5,868,740 A | 2/1999 | LeVeen et al. |
| 5,671,695 | A | 9/1997 | Schroeder | 5,868,789 A | 2/1999 | Huebner |
| 5,674,224 | A | 10/1997 | Howell et al. | 5,871,484 A | 2/1999 | Spievack et al. |
| 5,679,723 | A | 10/1997 | Cooper et al. | 5,871,486 A | 2/1999 | Huebner et al. |
| 5,681,352 | A | 10/1997 | Clancy, III et al. | 5,871,490 A | 2/1999 | Schulze et al. |
| 5,683,419 | A | 11/1997 | Thal | 5,885,294 A | 3/1999 | Pedlick et al. |
| 5,688,285 | A | 11/1997 | Yamada et al. | 5,891,168 A | 4/1999 | Thal |
| 5,690,676 | A | 11/1997 | DiPoto et al. | 5,893,592 A | 4/1999 | Schulze et al. |
| 5,690,678 | A | 11/1997 | Johnson | 5,895,395 A | 4/1999 | Yeung |
| 5,695,497 | A | 12/1997 | Stahelin et al. | 5,897,564 A | 4/1999 | Schulze et al. |
| 5,697,929 | A | 12/1997 | Mellinger | 5,897,574 A | 4/1999 | Bonutti |
| 5,699,657 | A * | 12/1997 | Paulson ........................ 57/22 | 5,899,902 A | 5/1999 | Brown et al. |
| 5,702,397 | A | 12/1997 | Goble et al. | 5,899,938 A | 5/1999 | Sklar et al. |
| 5,702,422 | A | 12/1997 | Stone | 5,908,421 A | 6/1999 | Beger et al. |

| | | | | | | |
|---|---|---|---|---|---|---|
| 5,908,436 A | 6/1999 | Cuschieri et al. | | 6,117,162 A | 9/2000 | Schmieding et al. |
| 5,910,148 A | 6/1999 | Reimels et al. | | 6,123,710 A | 9/2000 | Pinczewski et al. |
| 5,911,721 A | 6/1999 | Nicholson et al. | | 6,132,433 A | 10/2000 | Whelan |
| 5,918,604 A | 7/1999 | Whelan | | 6,132,437 A | 10/2000 | Omurtag et al. |
| 5,921,986 A | 7/1999 | Bonutti | | 6,139,565 A | 10/2000 | Stone et al. |
| 5,925,008 A | 7/1999 | Douglas | | RE36,974 E | 11/2000 | Bonutti |
| 5,928,267 A | 7/1999 | Bonutti et al. | | 6,143,017 A | 11/2000 | Thal |
| 5,931,838 A | 8/1999 | Vito | | 6,146,406 A | 11/2000 | Shluzas et al. |
| 5,931,844 A | 8/1999 | Thompson et al. | | 6,146,408 A | 11/2000 | Bartlett |
| 5,931,869 A | 8/1999 | Boucher et al. | | 6,149,653 A | 11/2000 | Deslauriers |
| 5,935,149 A | 8/1999 | Ek | | 6,149,669 A | 11/2000 | Li |
| 5,938,668 A | 8/1999 | Scirica et al. | | 6,152,928 A | 11/2000 | Wenstrom, Jr. |
| 5,941,439 A | 8/1999 | Kammerer et al. | | 6,152,934 A | 11/2000 | Harper et al. |
| 5,941,900 A | 8/1999 | Bonutti | | 6,152,936 A | 11/2000 | Christy et al. |
| 5,944,739 A | 8/1999 | Zlock et al. | | 6,152,949 A | 11/2000 | Bonutti |
| 5,946,783 A | 9/1999 | Plociennik et al. | | 6,156,039 A | 12/2000 | Thal |
| 5,947,915 A | 9/1999 | Thibodo, Jr. | | 6,156,056 A | 12/2000 | Kearns et al. |
| 5,947,982 A | 9/1999 | Duran | | 6,159,234 A | 12/2000 | Bonutti et al. |
| 5,948,002 A | 9/1999 | Bonutti | | 6,165,203 A | 12/2000 | Krebs |
| 5,951,559 A | 9/1999 | Burkhart | | 6,168,598 B1 | 1/2001 | Martello |
| 5,951,560 A | 9/1999 | Simon et al. | | 6,168,628 B1 | 1/2001 | Huebner |
| 5,954,747 A | 9/1999 | Clark | | 6,187,025 B1 | 2/2001 | Machek |
| 5,957,953 A | 9/1999 | DiPoto et al. | | 6,190,401 B1 | 2/2001 | Green et al. |
| 5,961,521 A | 10/1999 | Roger et al. | | 6,190,411 B1 | 2/2001 | Lo et al. |
| 5,961,524 A | 10/1999 | Crombie | | 6,193,754 B1 | 2/2001 | Seedhom |
| 5,964,764 A | 10/1999 | West, Jr. et al. | | 6,200,329 B1 | 3/2001 | Fung et al. |
| 5,964,767 A | 10/1999 | Tapia et al. | | 6,200,330 B1 | 3/2001 | Benderev et al. |
| 5,964,783 A | 10/1999 | Grafton et al. | | 6,203,565 B1 | 3/2001 | Bonutti et al. |
| 5,968,045 A | 10/1999 | Frazier | | 6,203,572 B1 * | 3/2001 | Johnson et al. .......... 623/13.15 |
| 5,968,047 A | 10/1999 | Reed | | 6,206,883 B1 | 3/2001 | Tunc |
| 5,976,125 A | 11/1999 | Graham | | 6,210,376 B1 | 4/2001 | Grayson |
| 5,976,127 A | 11/1999 | Lax | | 6,214,012 B1 | 4/2001 | Karpman et al. |
| 5,980,524 A | 11/1999 | Justin et al. | | 6,221,107 B1 | 4/2001 | Steiner et al. |
| 5,980,558 A | 11/1999 | Wiley | | 6,228,096 B1 | 5/2001 | Marchand |
| 5,980,559 A | 11/1999 | Bonutti | | 6,231,592 B1 | 5/2001 | Bonutti et al. |
| 5,989,252 A | 11/1999 | Fumex et al. | | 6,235,057 B1 | 5/2001 | Roger et al. |
| 5,989,256 A | 11/1999 | Kuslich et al. | | 6,238,395 B1 | 5/2001 | Bonutti |
| 5,989,282 A | 11/1999 | Bonutti | | 6,241,747 B1 | 6/2001 | Ruff |
| 5,993,452 A | 11/1999 | Vandewalle | | 6,241,771 B1 | 6/2001 | Gresser et al. |
| 5,997,542 A | 12/1999 | Burke | | 6,245,081 B1 | 6/2001 | Bowman et al. |
| 5,997,552 A | 12/1999 | Person et al. | | 6,258,091 B1 | 7/2001 | Sevrain et al. |
| 6,001,100 A | 12/1999 | Sherman et al. | | 6,267,766 B1 | 7/2001 | Burkhart |
| 6,007,567 A | 12/1999 | Bonutti | | 6,269,716 B1 | 8/2001 | Amis |
| 6,010,525 A | 1/2000 | Bonutti et al. | | 6,270,518 B1 | 8/2001 | Pedlick et al. |
| 6,016,727 A | 1/2000 | Morgan | | 6,273,890 B1 | 8/2001 | Frazier |
| 6,022,352 A | 2/2000 | Vandewalle | | 6,283,973 B1 | 9/2001 | Hubbard et al. |
| 6,022,373 A | 2/2000 | Li | | 6,283,996 B1 | 9/2001 | Chervitz et al. |
| 6,024,758 A | 2/2000 | Thal | | 6,287,325 B1 | 9/2001 | Bonutti |
| 6,027,523 A | 2/2000 | Schmieding | | 6,293,961 B2 | 9/2001 | Schwartz et al. |
| 6,033,430 A | 3/2000 | Bonutti | | 6,296,659 B1 * | 10/2001 | Foerster ...................... 606/224 |
| 6,039,753 A | 3/2000 | Meislin | | 6,299,615 B1 | 10/2001 | Huebner |
| 6,042,601 A | 3/2000 | Smith | | 6,302,888 B1 | 10/2001 | Mellinger et al. |
| 6,045,551 A | 4/2000 | Bonutti | | 6,306,156 B1 | 10/2001 | Clark |
| 6,045,573 A | 4/2000 | Wenstrom, Jr. et al. | | 6,306,159 B1 | 10/2001 | Schwartz et al. |
| 6,045,574 A | 4/2000 | Thal | | 6,309,405 B1 | 10/2001 | Bonutti |
| 6,048,343 A | 4/2000 | Mathis et al. | | 6,312,448 B1 | 11/2001 | Bonutti |
| 6,051,006 A | 4/2000 | Shluzas et al. | | 6,319,271 B1 | 11/2001 | Schwartz et al. |
| 6,053,916 A | 4/2000 | Moore | | 6,328,758 B1 | 12/2001 | Tornier et al. |
| 6,056,752 A | 5/2000 | Roger | | 6,342,060 B1 | 1/2002 | Adams |
| 6,056,772 A | 5/2000 | Bonutti | | 6,343,531 B2 | 2/2002 | Amis |
| 6,056,773 A | 5/2000 | Bonutti | | 6,364,897 B1 | 4/2002 | Bonutti |
| 6,059,817 A | 5/2000 | Bonutti et al. | | 6,368,322 B1 | 4/2002 | Luks et al. |
| 6,068,648 A | 5/2000 | Cole et al. | | 6,368,326 B1 | 4/2002 | Dakin et al. |
| 6,074,403 A | 6/2000 | Nord | | 6,368,343 B1 | 4/2002 | Bonutti et al. |
| 6,077,277 A | 6/2000 | Mollenauer et al. | | 6,371,124 B1 | 4/2002 | Whelan |
| 6,077,292 A | 6/2000 | Bonutti | | 6,379,361 B1 | 4/2002 | Beck, Jr. et al. |
| 6,086,591 A | 7/2000 | Bojarski | | 6,383,199 B2 | 5/2002 | Carter et al. |
| 6,086,592 A | 7/2000 | Rosenberg et al. | | 6,387,113 B1 | 5/2002 | Hawkins et al. |
| 6,086,608 A | 7/2000 | Ek et al. | | 6,387,129 B2 | 5/2002 | Rieser et al. |
| 6,096,060 A | 8/2000 | Fitts et al. | | 6,398,785 B2 | 6/2002 | Carchidi et al. |
| 6,099,530 A | 8/2000 | Simonian et al. | | 6,409,743 B1 | 6/2002 | Fenton, Jr. |
| 6,099,568 A | 8/2000 | Simonian et al. | | 6,413,260 B1 | 7/2002 | Berrevoets et al. |
| 6,117,160 A | 9/2000 | Bonutti | | 6,423,088 B1 | 7/2002 | Fenton, Jr. |

| Patent No. | Date | Inventor |
|---|---|---|
| 6,428,562 B2 | 8/2002 | Bonutti |
| 6,432,123 B2 | 8/2002 | Schwartz et al. |
| 6,436,124 B1 | 8/2002 | Anderson et al. |
| 6,440,134 B1 | 8/2002 | Zaccherotti et al. |
| 6,440,136 B1 | 8/2002 | Gambale et al. |
| 6,447,516 B1 | 9/2002 | Bonutti |
| 6,451,030 B2 | 9/2002 | Li et al. |
| 6,454,768 B1 | 9/2002 | Jackson |
| 6,458,134 B1 | 10/2002 | Songer et al. |
| 6,461,373 B2 | 10/2002 | Wyman et al. |
| 6,464,713 B2 | 10/2002 | Bonutti |
| 6,468,293 B2 | 10/2002 | Bonutti et al. |
| 6,471,707 B1 | 10/2002 | Miller et al. |
| 6,475,230 B1 | 11/2002 | Bonutti et al. |
| 6,482,210 B1 | 11/2002 | Skiba et al. |
| 6,485,504 B1 | 11/2002 | Johnson et al. |
| 6,497,901 B1 | 12/2002 | Royer |
| 6,500,184 B1 | 12/2002 | Chan et al. |
| 6,500,195 B2 | 12/2002 | Bonutti |
| RE37,963 E | 1/2003 | Thal |
| 6,503,267 B2 | 1/2003 | Bonutti et al. |
| 6,508,820 B2 | 1/2003 | Bales |
| 6,508,821 B1 | 1/2003 | Schwartz et al. |
| 6,508,830 B2 | 1/2003 | Steiner |
| 6,511,498 B1 * | 1/2003 | Fumex ............... 606/232 |
| 6,511,499 B2 | 1/2003 | Schmieding et al. |
| 6,517,542 B1 | 2/2003 | Papay et al. |
| 6,517,552 B1 | 2/2003 | Nord et al. |
| 6,517,578 B2 * | 2/2003 | Hein ............... 623/13.13 |
| 6,517,579 B1 | 2/2003 | Paulos et al. |
| 6,520,964 B2 | 2/2003 | Tallarida et al. |
| 6,520,980 B1 | 2/2003 | Foerster |
| 6,524,317 B1 | 2/2003 | Ritchart et al. |
| 6,527,777 B2 | 3/2003 | Justin |
| 6,527,794 B1 | 3/2003 | McDevitt et al. |
| 6,527,795 B1 | 3/2003 | Lizardi |
| 6,533,795 B1 | 3/2003 | Tran et al. |
| 6,533,802 B2 | 3/2003 | Bojarski et al. |
| 6,537,319 B2 | 3/2003 | Whelan |
| 6,540,750 B2 | 4/2003 | Burkhart |
| 6,540,770 B1 | 4/2003 | Tornier et al. |
| 6,544,281 B2 | 4/2003 | ElAttrache et al. |
| 6,547,564 B1 | 4/2003 | Hansson et al. |
| 6,547,800 B2 | 4/2003 | Foerster et al. |
| 6,551,330 B1 | 4/2003 | Bain et al. |
| 6,551,343 B1 | 4/2003 | Tormala et al. |
| 6,554,830 B1 | 4/2003 | Chappius |
| 6,554,852 B1 | 4/2003 | Oberlander |
| 6,554,862 B2 | 4/2003 | Hays et al. |
| 6,562,071 B2 | 5/2003 | Jarvinen et al. |
| 6,565,572 B2 | 5/2003 | Chappius |
| 6,565,573 B1 | 5/2003 | Ferrante et al. |
| 6,569,186 B1 | 5/2003 | Winters et al. |
| 6,569,187 B1 | 5/2003 | Bonutti et al. |
| 6,572,635 B1 | 6/2003 | Bonutti |
| 6,575,925 B1 | 6/2003 | Noble |
| 6,579,295 B1 | 6/2003 | Supinski |
| 6,582,453 B1 | 6/2003 | Tran et al. |
| 6,585,730 B1 | 7/2003 | Foerster |
| 6,585,740 B2 | 7/2003 | Schlapfer et al. |
| 6,585,750 B2 | 7/2003 | Bonutti et al. |
| 6,589,245 B1 | 7/2003 | Weiler et al. |
| 6,589,246 B1 | 7/2003 | Hack et al. |
| 6,592,609 B1 | 7/2003 | Bonutti |
| 6,595,911 B2 | 7/2003 | LoVuolo |
| 6,599,289 B1 | 7/2003 | Bojarski et al. |
| 6,605,096 B1 | 8/2003 | Ritchart |
| 6,607,548 B2 | 8/2003 | Pohjonen et al. |
| 6,616,694 B1 | 9/2003 | Hart |
| 6,620,166 B1 | 9/2003 | Wenstrom, Jr. et al. |
| 6,620,185 B1 | 9/2003 | Harvie et al. |
| 6,620,195 B2 | 9/2003 | Goble et al. |
| 6,620,329 B2 | 9/2003 | Rosen et al. |
| 6,620,349 B1 | 9/2003 | Lopez |
| 6,623,492 B1 | 9/2003 | Berube et al. |
| 6,623,524 B2 | 9/2003 | Schmieding |
| 6,626,910 B1 | 9/2003 | Hogues |
| 6,626,919 B1 | 9/2003 | Swanstrom |
| 6,629,977 B1 | 10/2003 | Wolf |
| 6,635,073 B2 | 10/2003 | Bonutti |
| 6,638,279 B2 | 10/2003 | Bonutti |
| 6,641,596 B1 | 11/2003 | Lizardi |
| 6,641,597 B2 | 11/2003 | Burkhart et al. |
| 6,645,227 B2 | 11/2003 | Fallin et al. |
| 6,652,562 B2 | 11/2003 | Collier et al. |
| 6,652,563 B2 | 11/2003 | Dreyfuss |
| 6,656,182 B1 | 12/2003 | Hayhurst |
| 6,656,183 B2 | 12/2003 | Colleran et al. |
| 6,658,182 B1 | 12/2003 | Gonthier et al. |
| 6,660,008 B1 | 12/2003 | Foerster et al. |
| 6,660,022 B1 | 12/2003 | Li et al. |
| 6,663,634 B2 | 12/2003 | Ahrens et al. |
| 6,663,656 B2 | 12/2003 | Schmieding et al. |
| 6,666,868 B2 | 12/2003 | Fallin |
| 6,682,549 B2 | 1/2004 | Bartlett |
| 6,685,728 B2 | 2/2004 | Sinnott et al. |
| 6,689,137 B2 | 2/2004 | Reed |
| 6,689,154 B2 | 2/2004 | Bartlett |
| 6,692,499 B2 | 2/2004 | Tormala et al. |
| 6,712,849 B2 | 3/2004 | Re et al. |
| 6,716,224 B2 | 4/2004 | Singhatat |
| 6,716,957 B2 | 4/2004 | Tunc |
| 6,730,092 B2 | 5/2004 | Songer |
| 6,730,124 B2 | 5/2004 | Steiner |
| 6,746,483 B1 | 6/2004 | Bojarski et al. |
| 6,755,836 B1 | 6/2004 | Lewis |
| 6,761,739 B2 | 7/2004 | Shepard |
| 6,767,037 B2 | 7/2004 | Wenstrom, Jr. |
| 6,770,076 B2 | 8/2004 | Foerster |
| 6,770,084 B1 | 8/2004 | Bain et al. |
| 6,773,450 B2 | 8/2004 | Leung et al. |
| 6,780,190 B2 | 8/2004 | Maroney |
| 6,780,198 B1 | 8/2004 | Gregoire et al. |
| 6,802,862 B1 | 10/2004 | Roger et al. |
| 6,808,502 B2 | 10/2004 | Nguyen et al. |
| 6,808,526 B1 | 10/2004 | Magerl et al. |
| 6,814,741 B2 | 11/2004 | Bowman et al. |
| 6,830,572 B2 | 12/2004 | McDevitt et al. |
| 6,833,005 B1 | 12/2004 | Mantas et al. |
| 6,840,953 B2 | 1/2005 | Martinek |
| 6,860,885 B2 | 3/2005 | Bonutti |
| 6,863,671 B1 | 3/2005 | Strobel et al. |
| 6,872,040 B2 | 3/2005 | Deeg et al. |
| 6,875,216 B2 | 4/2005 | Wolf |
| 6,884,249 B2 | 4/2005 | May et al. |
| 6,887,259 B2 | 5/2005 | Lizardi |
| 6,890,354 B2 | 5/2005 | Steiner et al. |
| 6,893,448 B2 | 5/2005 | O'Quinn et al. |
| 6,896,686 B2 | 5/2005 | Weber |
| 6,899,722 B2 | 5/2005 | Bonutti |
| 6,902,573 B2 | 6/2005 | Strobel et al. |
| 6,908,466 B1 | 6/2005 | Bonutti et al. |
| 6,916,321 B2 | 7/2005 | TenHuisen et al. |
| 6,921,402 B2 | 7/2005 | Contiliano et al. |
| 6,923,823 B1 | 8/2005 | Bartlett et al. |
| 6,923,824 B2 | 8/2005 | Morgan et al. |
| 6,951,565 B2 | 10/2005 | Keane et al. |
| 6,972,027 B2 | 12/2005 | Fallin et al. |
| 6,980,903 B2 | 12/2005 | Daniels et al. |
| 6,986,781 B2 | 1/2006 | Smith |
| 6,989,034 B2 | 1/2006 | Hammer et al. |
| 7,066,944 B2 | 6/2006 | Laufer et al. |
| 7,105,010 B2 | 9/2006 | Hart et al. |
| 7,112,221 B2 | 9/2006 | Harris et al. |
| 7,118,583 B2 | 10/2006 | O'Quinn et al. |
| 7,137,996 B2 | 11/2006 | Steiner et al. |

| | | |
|---|---|---|
| 7,141,066 B2 | 11/2006 | Steiner et al. |
| 7,153,312 B1 | 12/2006 | Torrie et al. |
| 7,261,716 B2 | 8/2007 | Strobel et al. |
| 2001/0014825 A1 | 8/2001 | Burke et al. |
| 2001/0037131 A1 | 11/2001 | Schmieding et al. |
| 2001/0037153 A1 | 11/2001 | Rockwood et al. |
| 2001/0041937 A1 | 11/2001 | Rieser et al. |
| 2001/0041938 A1* | 11/2001 | Hein .................. 623/13.13 |
| 2001/0044639 A1 | 11/2001 | Levinson |
| 2001/0047206 A1 | 11/2001 | Sklar et al. |
| 2001/0051816 A1 | 12/2001 | Enzerink et al. |
| 2001/0053934 A1 | 12/2001 | Schmieding |
| 2002/0001964 A1 | 1/2002 | Choi |
| 2002/0004669 A1 | 1/2002 | Bartlett |
| 2002/0007182 A1 | 1/2002 | Kim |
| 2002/0010513 A1 | 1/2002 | Schmieding |
| 2002/0013608 A1 | 1/2002 | ElAttrache et al. |
| 2002/0019649 A1 | 2/2002 | Sikora et al. |
| 2002/0055780 A1 | 5/2002 | Sklar |
| 2002/0058966 A1 | 5/2002 | Tormala et al. |
| 2002/0099411 A1 | 7/2002 | Bartlett |
| 2002/0111653 A1 | 8/2002 | Foerster |
| 2002/0120292 A1* | 8/2002 | Morgan .................. 606/232 |
| 2002/0123752 A1 | 9/2002 | Schultheiss et al. |
| 2002/0128684 A1 | 9/2002 | Foerster |
| 2002/0147463 A1 | 10/2002 | Martinek |
| 2002/0161401 A1 | 10/2002 | Steiner |
| 2002/0161439 A1 | 10/2002 | Strobel |
| 2002/0169452 A1 | 11/2002 | Tormala et al. |
| 2002/0169478 A1 | 11/2002 | Schwartz et al. |
| 2002/0173788 A1 | 11/2002 | Bojarski et al. |
| 2002/0188298 A1 | 12/2002 | Chan |
| 2003/0023268 A1 | 1/2003 | Lizardi |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0065391 A1 | 4/2003 | Re et al. |
| 2003/0078617 A1 | 4/2003 | Schwartz et al. |
| 2003/0083662 A1 | 5/2003 | Middleton |
| 2003/0088251 A1 | 5/2003 | Braun et al. |
| 2003/0088272 A1 | 5/2003 | Smith |
| 2003/0105477 A1 | 6/2003 | Schwartz et al. |
| 2003/0120309 A1 | 6/2003 | Colleran et al. |
| 2003/0130694 A1 | 7/2003 | Bojarski et al. |
| 2003/0135214 A1 | 7/2003 | Fetto et al. |
| 2003/0135239 A1 | 7/2003 | Gabriel et al. |
| 2003/0135963 A1 | 7/2003 | Holbrook et al. |
| 2003/0152522 A1 | 8/2003 | Miller et al. |
| 2003/0167072 A1 | 9/2003 | Oberlander |
| 2003/0167090 A1 | 9/2003 | Chervitz et al. |
| 2003/0171811 A1 | 9/2003 | Steiner et al. |
| 2003/0176865 A1 | 9/2003 | Supinski |
| 2003/0176919 A1 | 9/2003 | Schmieding |
| 2003/0181925 A1 | 9/2003 | Bain et al. |
| 2003/0195528 A1 | 10/2003 | Ritchart |
| 2003/0225459 A1 | 12/2003 | Hammer et al. |
| 2004/0002734 A1 | 1/2004 | Fallin et al. |
| 2004/0006345 A1 | 1/2004 | Vlahos et al. |
| 2004/0006346 A1 | 1/2004 | Holmen et al. |
| 2004/0015171 A1 | 1/2004 | Bojarski et al. |
| 2004/0015172 A1 | 1/2004 | Biedermann et al. |
| 2004/0024456 A1 | 2/2004 | Brown et al. |
| 2004/0087981 A1 | 5/2004 | Berube et al. |
| 2004/0092936 A1 | 5/2004 | Miller et al. |
| 2004/0098051 A1 | 5/2004 | Fallin et al. |
| 2004/0111117 A1 | 6/2004 | Colleran et al. |
| 2004/0122431 A1 | 6/2004 | Biedermann et al. |
| 2004/0138664 A1 | 7/2004 | Bowman |
| 2004/0138704 A1 | 7/2004 | Gambale et al. |
| 2004/0138706 A1 | 7/2004 | Abrams et al. |
| 2004/0143344 A1 | 7/2004 | Malaviya et al. |
| 2004/0153103 A1 | 8/2004 | Schwartz et al. |
| 2004/0153153 A1 | 8/2004 | Elson et al. |
| 2004/0162579 A1 | 8/2004 | Foerster |
| 2004/0166169 A1 | 8/2004 | Malaviya et al. |
| 2004/0182968 A1 | 9/2004 | Gentry |
| 2004/0220574 A1 | 11/2004 | Pelo et al. |
| 2004/0225292 A1 | 11/2004 | Sasso et al. |
| 2004/0236353 A1 | 11/2004 | Bain et al. |
| 2004/0243139 A1 | 12/2004 | Lewis et al. |
| 2004/0243178 A1 | 12/2004 | Haut et al. |
| 2004/0249394 A1 | 12/2004 | Morris et al. |
| 2004/0267164 A1 | 12/2004 | Rhodes et al. |
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis et al. |
| 2004/0267304 A1 | 12/2004 | Zannis et al. |
| 2005/0027307 A1 | 2/2005 | Schwartz et al. |
| 2005/0033363 A1 | 2/2005 | Bojarski et al. |
| 2005/0038426 A1 | 2/2005 | Chan |
| 2005/0064042 A1 | 3/2005 | Vunjak-Novakovic et al. |
| 2005/0074495 A1 | 4/2005 | Schwartz et al. |
| 2005/0090828 A1 | 4/2005 | Alford |
| 2005/0096696 A1 | 5/2005 | Forsberg |
| 2005/0096697 A1 | 5/2005 | Forsberg et al. |
| 2005/0107828 A1 | 5/2005 | Reese |
| 2005/0119531 A1 | 6/2005 | Sharratt |
| 2005/0125073 A1 | 6/2005 | Orban et al. |
| 2005/0137600 A1 | 6/2005 | Jacobs et al. |
| 2005/0149033 A1 | 7/2005 | McGuire et al. |
| 2005/0159812 A1 | 7/2005 | Dinger et al. |
| 2005/0165416 A1 | 7/2005 | Bojarski et al. |
| 2005/0165482 A1 | 7/2005 | Goldhahn et al. |
| 2005/0222618 A1 | 10/2005 | Dreyfuss et al. |
| 2005/0222619 A1 | 10/2005 | Dreyfuss et al. |
| 2005/0228448 A1 | 10/2005 | Li |
| 2005/0267479 A1 | 12/2005 | Morgan et al. |
| 2005/0277961 A1 | 12/2005 | Stone et al. |
| 2005/0283156 A1 | 12/2005 | Schmieding et al. |
| 2005/0283158 A1 | 12/2005 | West |
| 2005/0283192 A1 | 12/2005 | Torrie et al. |
| 2006/0030948 A1 | 2/2006 | Manrique et al. |
| 2006/0036265 A1 | 2/2006 | Dant |
| 2006/0064126 A1 | 3/2006 | Fallin et al. |
| 2006/0069334 A1 | 3/2006 | Moskowitz |
| 2006/0100627 A1 | 5/2006 | Stone et al. |
| 2006/0121084 A1 | 6/2006 | Borden et al. |
| 2006/0135958 A1 | 6/2006 | Marissen et al. |
| 2006/0167482 A1 | 7/2006 | Swain et al. |
| 2006/0178680 A1 | 8/2006 | Nelson et al. |
| 2006/0189993 A1 | 8/2006 | Stone |
| 2006/0190042 A1 | 8/2006 | Stone et al. |
| 2006/0229671 A1 | 10/2006 | Steiner et al. |
| 2006/0247642 A1 | 11/2006 | Stone et al. |
| 2006/0271192 A1 | 11/2006 | Olsen et al. |
| 2006/0282085 A1 | 12/2006 | Stone et al. |
| 2006/0293709 A1 | 12/2006 | Bojarski et al. |
| 2007/0016305 A1 | 1/2007 | Chudik |
| 2007/0055255 A1 | 3/2007 | Siegel |
| 2007/0078435 A1 | 4/2007 | Stone et al. |
| 2007/0083236 A1 | 4/2007 | Sikora et al. |
| 2007/0185532 A1 | 8/2007 | Stone et al. |
| 2008/0027446 A1 | 1/2008 | Stone et al. |
| 2008/0065114 A1 | 3/2008 | Stone et al. |
| 2008/0082127 A1 | 4/2008 | Stone et al. |
| 2008/0082128 A1 | 4/2008 | Stone |
| 2008/0132932 A1 | 6/2008 | Hoeppner et al. |
| 2008/0140092 A1 | 6/2008 | Stone et al. |
| 2008/0140093 A1 | 6/2008 | Stone et al. |
| 2008/0161852 A1 | 7/2008 | Kaiser et al. |
| 2008/0255613 A1 | 10/2008 | Kaiser et al. |

2009/0082805 A1   3/2009   Kaiser et al.

FOREIGN PATENT DOCUMENTS

| Country | Number | Date |
|---|---|---|
| AU | 8963869 | 2/1971 |
| AU | 1505470 | 11/1971 |
| AU | 3615171 | 5/1973 |
| AU | 7110887 | 10/1987 |
| AU | 639410 | 11/1989 |
| AU | 651929 | 8/1994 |
| DE | 2529669 | 3/1976 |
| DE | 2747312 | 4/1979 |
| DE | 2818254 | 10/1979 |
| DE | 2919009 | 11/1979 |
| DE | 3027138 | 12/1981 |
| DE | 3225620 | 2/1983 |
| DE | 3136083 | 3/1983 |
| DE | 233303 | 2/1986 |
| DE | 4127550 | 2/1993 |
| DE | 4302397 | 7/1993 |
| DE | 29621340 | 5/1998 |
| DE | 19841252 | 3/2000 |
| EP | 0108912 | 5/1984 |
| EP | 0 129 442 | 12/1984 |
| EP | 0 172 130 | 2/1986 |
| EP | 0 241 240 | 10/1987 |
| EP | 0 241 792 | 10/1987 |
| EP | 0 260 970 | 3/1988 |
| EP | 0270704 | 6/1988 |
| EP | 0 282 789 | 9/1988 |
| EP | 0 317 406 | 5/1989 |
| EP | 0315371 | 5/1989 |
| EP | 0340159 | 11/1989 |
| EP | 0 346 183 | 12/1989 |
| EP | 0 349 173 | 1/1990 |
| EP | 0 374 088 | 6/1990 |
| EP | 0409364 | 1/1991 |
| EP | 0415915 | 3/1991 |
| EP | 0440991 | 8/1991 |
| EP | 0441065 | 8/1991 |
| EP | 0 451 932 | 10/1991 |
| EP | 0 464 480 | 1/1992 |
| EP | 0502509 | 9/1992 |
| EP | 0502698 | 9/1992 |
| EP | 520177 | 12/1992 |
| EP | 0 497 079 | 6/1993 |
| EP | 0 546 726 | 6/1993 |
| EP | 0574707 | 12/1993 |
| EP | 0 582 514 | 2/1994 |
| EP | 0591991 | 4/1994 |
| EP | 0598219 | 5/1994 |
| EP | 0 627 203 | 12/1994 |
| EP | 0651979 | 5/1995 |
| EP | 0669110 | 8/1995 |
| EP | 0686373 | 12/1995 |
| EP | 0702933 | 3/1996 |
| EP | 0775473 | 5/1997 |
| EP | 0913123 | 5/1999 |
| EP | 0913131 | 5/1999 |
| EP | 99121106 | 10/1999 |
| EP | 991210527 | 10/1999 |
| EP | 0995409 | 4/2000 |
| EP | 1013229 | 6/2000 |
| EP | 1093773 | 4/2001 |
| EP | 1093774 | 4/2001 |
| EP | 1555945 | 7/2005 |
| FR | 2 622 790 | 5/1989 |
| FR | 2 655 840 | 6/1991 |
| FR | 2682867 | 4/1993 |
| FR | 2 687 911 | 9/1993 |
| FR | 2 688 689 | 9/1993 |
| FR | 2 704 140 | 10/1994 |
| FR | 2717070 | 9/1995 |
| FR | 2723528 | 2/1996 |
| FR | 2744010 | 8/1997 |
| FR | 2745999 | 9/1997 |
| FR | 2770764 | 5/1999 |
| GB | 401677 | 11/1933 |
| GB | 1413477 | 11/1975 |
| GB | 1485681 | 9/1977 |
| GB | 2083751 | 3/1982 |
| GB | 2 118 474 | 11/1983 |
| GB | 2 227 175 | 7/1990 |
| GB | 2 253 147 | 9/1992 |
| GB | 2312376 | 10/1997 |
| JP | 5362911 | 5/1978 |
| JP | 5362912 | 5/1978 |
| JP | 5374942 | 6/1978 |
| JP | 5378230 | 6/1978 |
| JP | 62159647 | 7/1987 |
| JP | 62295657 | 12/1987 |
| JP | 5269160 | 10/1993 |
| JP | 5300917 | 11/1993 |
| JP | 751292 | 2/1995 |
| JP | 10211213 | 8/1998 |
| WO | WO-8300615 | 3/1983 |
| WO | WO 86/03666 | 7/1986 |
| WO | WO-8701270 | 3/1987 |
| WO | WO-8901767 | 3/1989 |
| WO | WO 89/09030 | 10/1989 |
| WO | WO 89/10096 | 11/1989 |
| WO | WO-8910096 | 11/1989 |
| WO | WO 90/08510 | 8/1990 |
| WO | WO 92/03980 | 3/1992 |
| WO | WO-9314705 | 8/1993 |
| WO | WO-9315694 | 8/1993 |
| WO | WO-9502373 | 1/1995 |
| WO | WO-9529637 | 11/1995 |
| WO | WO-9532670 | 12/1995 |
| WO | WO 96/29029 | 9/1996 |
| WO | WO-9737603 | 10/1997 |
| WO | WO 98/12991 | 4/1998 |
| WO | WO 98/12992 | 4/1998 |
| WO | WO-9822047 | 5/1998 |
| WO | WO-9822048 | 5/1998 |
| WO | WO-9901084 | 1/1999 |
| WO | WO-9912480 | 3/1999 |
| WO | WO-9944544 | 9/1999 |
| WO | WO-0040159 | 7/2000 |
| WO | WO-0139671 | 6/2001 |
| WO | WO-0236020 | 5/2002 |
| WO | WO-03071962 | 9/2003 |
| WO | WO-03077772 | 9/2003 |
| WO | WO-2005104992 | 11/2005 |

OTHER PUBLICATIONS

"Technique for ACL Reconstruction with Acufex Director Drill Guide and Endobutton CL," by Thomas D. Roseberg, copyright 1999 Smith & Nephew.

"SE Graft Tensioning System Surgical Technique," Linvatec Corporation copyright 2003, 2004.

Bio-Intrafix (TCP/PLA) & Intrafix, Tibial Soft Tissue Fasteners, by DePuy Mitek, 6 sheets, (date unknown).

"PANALOK Anchor with PDS II and ETHIBOND Suture", Mitek Products ETHICON, 1997.

A. Weiler, et al; Biodegradierbare Interferenzschrauben in der Kreuzbandchirurgie; OP-Journal 14 pp. 278-284; 1998.

Arthrotek, A Biomet Company; Knees; Sure fire Hybrid Meniscal Device.

Arthrotek, A Biomet Company; Sure fire Hybrid Meniscal Device; Launch Date: Fall AANA 2004.

F. Alan Barber, M.D., "Uses and Abuses of Sutures and Anchors," Shoulder Scope, San Diego Shoulder Arthroscopy Library.

F. Alan Barber, M.D., "Using Sutures and Anchors," San Diego Shoulder Arthroscopy Course, 17th Annual Meeting.

Flavia Namie Azato, et al. "Traction endurance biomechanical study of metallic suture anchors at different insertion angles," Acta ortop. bras., vol. 11, No. 1, Sao Paulo, Jan./Mar. 2003.

Hecker AT, et al., "Pull-out strength of suture anchors for rotator cuff and Bankart lesion repairs," Am J Sports Med. 1993.

Lawhorn, M.D., Keith, MaxFire™ Meniscal Repair Device with Zip Loop™ Technology, Biomet Sports Medicine, Feb. 29, 2008.

Mark D. Miller et al.; "Pitfalls Associated with FasT-Fix Meniscal Repair," Arthroscopy: The Journal of Arthroscopic and Related Surgery, vol. 18, No. 8 (Oct.), 2002: pp. 939-943.

Opus Medical; The AutoCuff System; www.opusmedical.com; 2003.

Patrick Hunt, et al.; Development of a Perforated Biodegradable Interference Screw; Arthroscopy: The Journal of Arthroscopic and Related Surgery, vol. 21, No. 3; pp. 258-265; Mar. 2005.

Roy Alan Majors, M.D.; "Meniscal repairs: proven techniques and current trends," Lippincott Williams & Wilkins, Inc.; 2002.

Shoulder Arthroscopy; pp. H-2-H-22.

Smith & Nephew Endoscopy, "Endoscopic Meniscal Repair Using the T-Fix;" 1996.

Smith & Nephew, "Fast-Fix," Meniscal Repair System; 2001.

Stuart E. Fromm, M.D., RapidLoc, Meniscal Repair System, Mitek Products, Ethicon, 2001.

ToggleLoc™ Femoral Fixation Device, Arthrotek, Mar. 31, 2006.

US 6,238,418, 05/2001, Schwartz et al. (withdrawn)

* cited by examiner

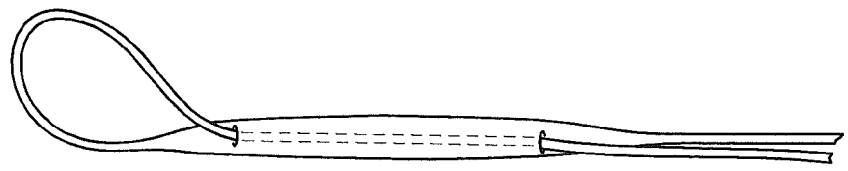
FIG. 1 (prior art)
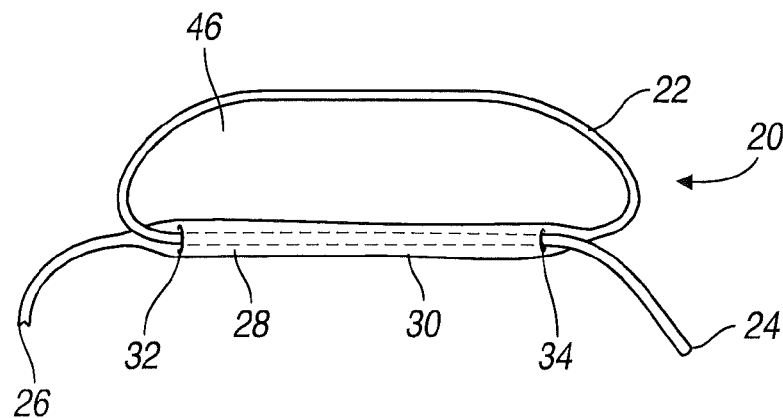
FIG. 2A
FIG. 2B
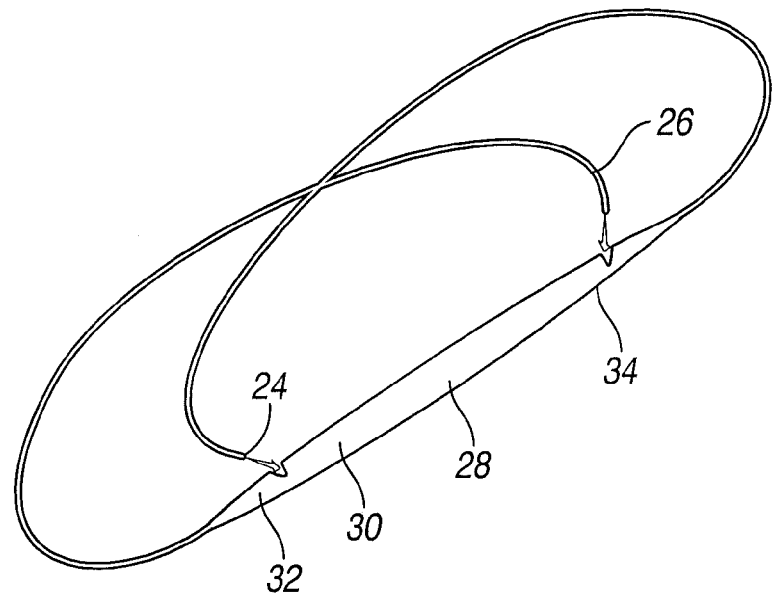
FIG. 3

METHOD AND APPARATUS FOR FORMING A SELF-LOCKING ADJUSTABLE SUTURE LOOP

FIELD

The present disclosure relates to method of implanting a prosthetic and, more particularly, to a method of implanting an ACL within a femoral tunnel.

BACKGROUND

The statements in this section merely provide background information related to the present disclosure and may not constitute prior art.

It is commonplace in arthroscopic procedures to employ sutures and anchors to secure soft tissues to bone. Despite their widespread use, several improvements in the use of sutures and suture anchors can be made. For example, the procedure of tying knots can be very time consuming, thereby increasing the cost of the procedure and limiting the capacity of the surgeon. Furthermore, the strength of the repair may be limited by the strength of the knot. This latter drawback may be of particular significance if the knot is tied improperly as the strength of the knot in such situations can be significantly lower than the tensile strength of the suture material.

To overcome this problem, sutures having a single preformed loop have been provided. FIG. 1 represents a prior art suture construction. As shown, one end of the suture is passed through a passage defined in the suture itself. The application of tension to the ends of the suture pulls a portion of the suture through the passage, causing a loop formed in the suture to close. Unfortunately, relaxation of the system can allow a portion of the suture to translate back through the passage, thus relieving the desired tension.

It is an object of the present teachings to provide an alternative device for anchoring sutures to bone and soft tissue. The device, which is relatively simple in design and structure, is highly effective for its intended purpose.

SUMMARY

To overcome the aforementioned deficiencies, a method for configuring a braided tubular suture and a suture configuration are disclosed. The method includes passing a first end of the suture through a first aperture into a passage defined by the suture and out a second aperture defined by the suture so as to place the first end outside of the passage. A second end of the suture is passed through the second aperture into the passage and out the first aperture so as to place the second end outside of the passage.

A method of surgically implanting a suture construction in a femoral tunnel is disclosed. A suture construction is formed by passing the suture through a bore defined by a locking member. A first end of the suture is passed through a first aperture within the suture into a passage defined by the suture and out a second aperture defined by the suture so as to place the first end outside of the passage and define a first loop. A second end of the suture is then passed through the second aperture into the passage and out the first aperture so as to place the second end outside of the passage, and define a second loop. The first and second ends and the first and second loops are then passed through the femoral tunnel. Soft tissue is then passed through the first and second loops. Tension is applied onto the first and second ends to constrict the first and second loops about the soft tissue.

In another embodiment, a method of surgically implanting a suture is disclosed. The suture is passed through a bore defined by a first fastener. A suture construction is formed by passing the suture through a bore defined by a locking member. A first end of the suture is passed through a first aperture within the suture into a passage defined by the suture and out a second aperture defined by the suture so as to place the first end outside of the passage and define a first loop. A second end of the suture is then passed through the second aperture into the passage and out the first aperture so as to place the second end outside of the passage, and define a second loop. A second fastener is coupled to at least one of the first and second loops. After the fastener is coupled to the patient, tension is applied onto the first and second ends to constrict at least one of the first and second loops.

In another embodiment a method of surgically implanting a soft tissue replacement for attaching two bone members is disclosed. A first and second tunnels are formed in first and second bones. A locking member having a first profile which allows insertion of the locking member through the tunnel and a second profile which allows engagement with the positive locking surface upon rotation of the locking member is provided. The suture construction described above is coupled to the locking member. The first and second ends and the first and second loops of the construction and the locking member are threaded through the first and second tunnels. Soft tissue is threaded through the first and second loops so as to engage bearing surfaces on the first and second loops. The locking member is then engaged.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 1 represents a prior art suture configuration;

FIGS. 2A and 2B represent suture constructions according to the teachings;

FIG. 3 represents the formation of the suture configuration shown in FIG. 2A;

DETAILED DESCRIPTION

Figure 4A:
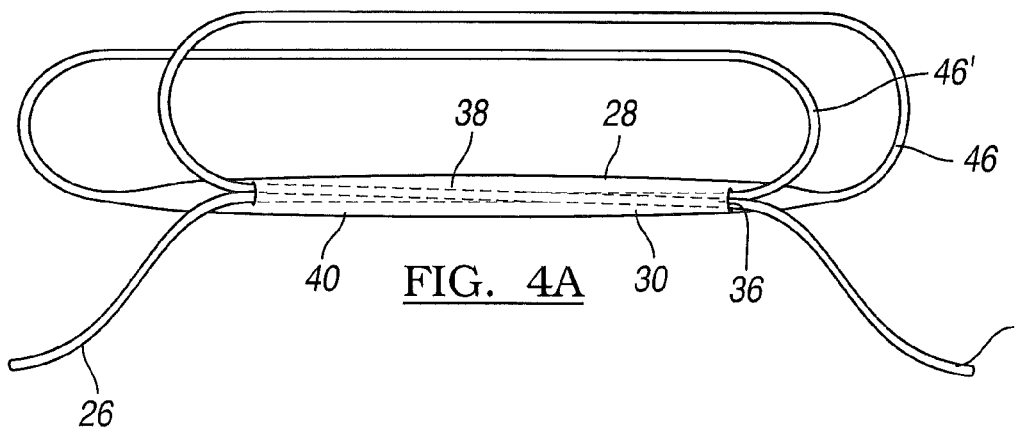
FIGS. 4A and 4B represent alternate suture configurations.

The following description is merely exemplary in nature and is not intended to limit the present disclosure, application, or uses. It should be understood that throughout the drawings, corresponding reference numerals indicate like or corresponding parts and features.

FIG. 2A represents a suture construction 20 according to the present teachings. Shown is a suture 22 having a first end 24 and a second end 26. The suture 22 is formed of a braided body 28 that defines a longitudinally formed hollow passage 30 therein. First and second apertures 32 and 34 are defined in the braided body 28 at first and second locations of the longitudinally formed passage 30.

Briefly referring to FIG. 3, a first end 24 of the suture 22 is passed through the first aperture 32 and through longitudinal passage 30 formed by a passage portion and out the second aperture 34. The second end 26 is passed through the second aperture 34, through the passage 30 and out the first aperture 32. This forms two loops 46 and 46'. As seen in FIG. 2B, the relationship of the first and second apertures 32 and 34 with respect to the first and second ends 24 and 26 can be modified so as to allow a bow-tie suture construction 36. As described below, the longitudinal and parallel placement of first and second suture portions 38 and 40 of the suture 22 within the longitudinal passage 30 resists the reverse relative movement of the first and second portions 38 and 40 of the suture once it is tightened.

The first and second apertures are formed during the braiding process as loose portions between pairs of fibers defining the suture. As further described below, the first and second ends 24 and 26 can be passed through the longitudinal passage 30 multiple times. It is envisioned that either a single or multiple apertures can be formed at the ends of the longitudinally formed passage.

Figure 4B:
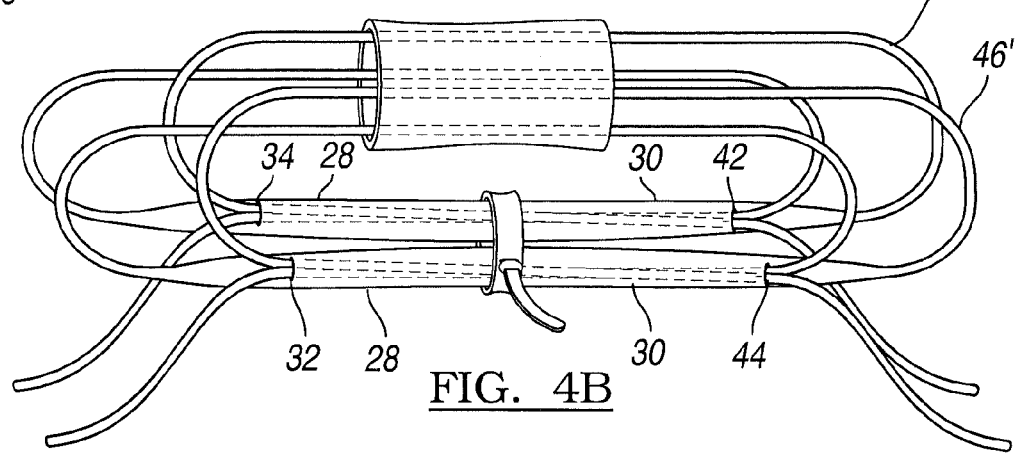

As best seen in FIGS. 4A and 4B, a portion of the braided body 28 of the suture defining the longitudinal passage 30 can be braided so as to have a diameter larger than the diameter of the first and second ends 24 and 26. Additionally shown are first through fourth apertures 32, 34, 42, and 44. These apertures can be formed in the braiding process or can be formed during the construction process. In this regard, the apertures 32, 34, 42, and 44 are defined between adjacent fibers in the braided body 28. As shown in FIG. 4B, and described below, it is envisioned the sutures can be passed through other biomedically compatible structures.

Figure 5:
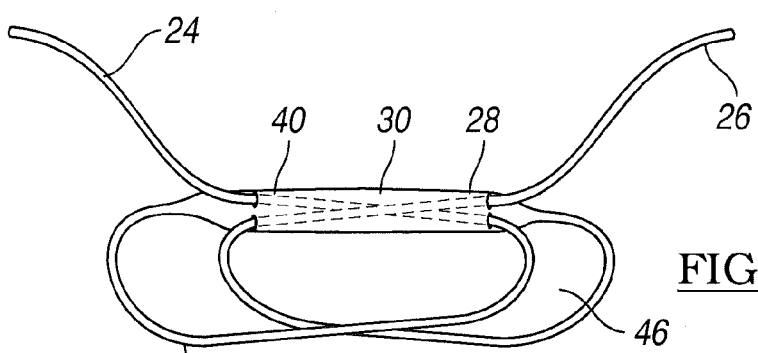
FIGS. 5-7 represent further alternate suture configurations.
Figure 6:
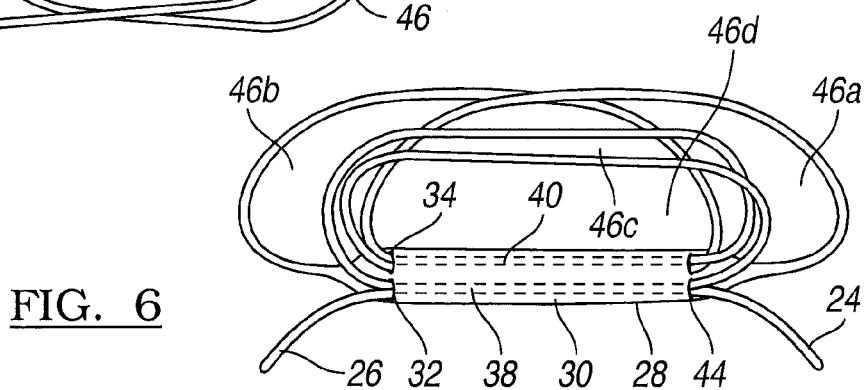
Figure 7:
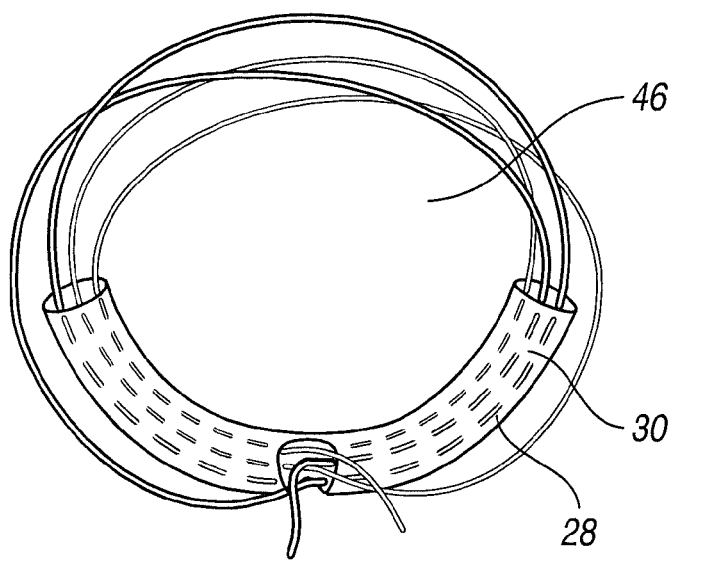
Figure 8:
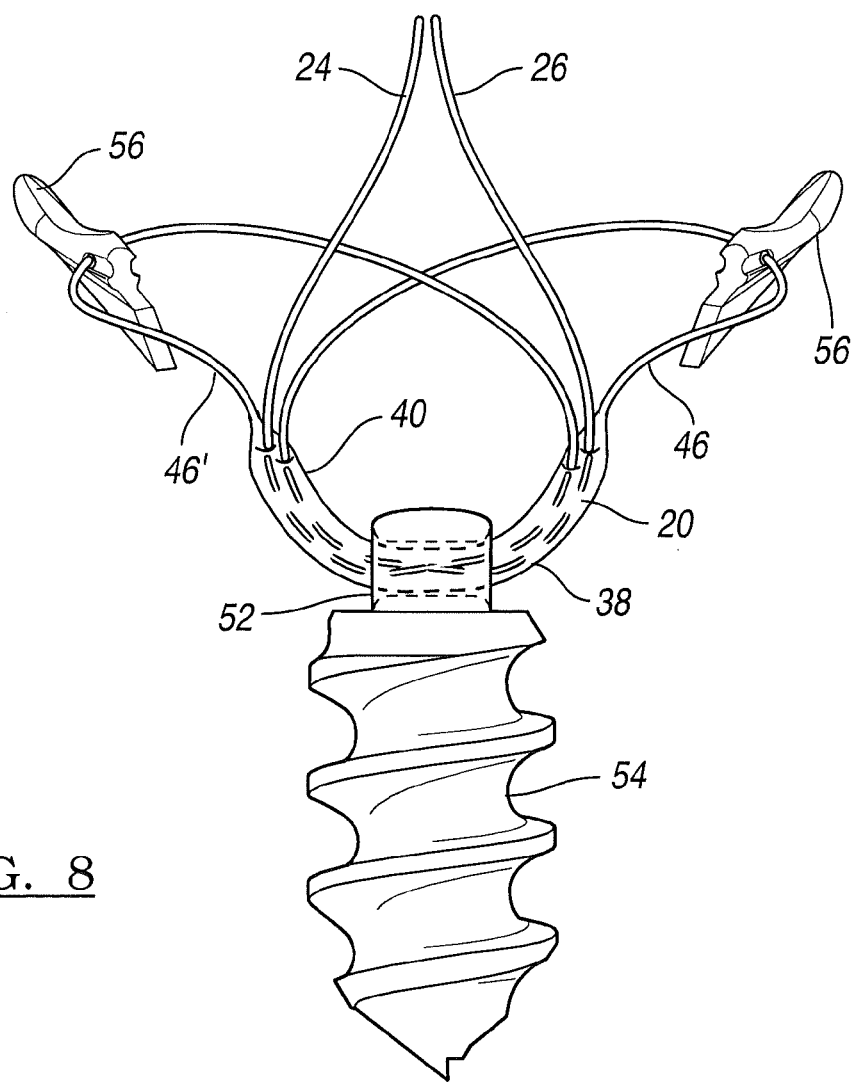
FIG. 8 represents the suture construction according to FIG. 5 coupled to a bone engaging fastener.
Figure 9:
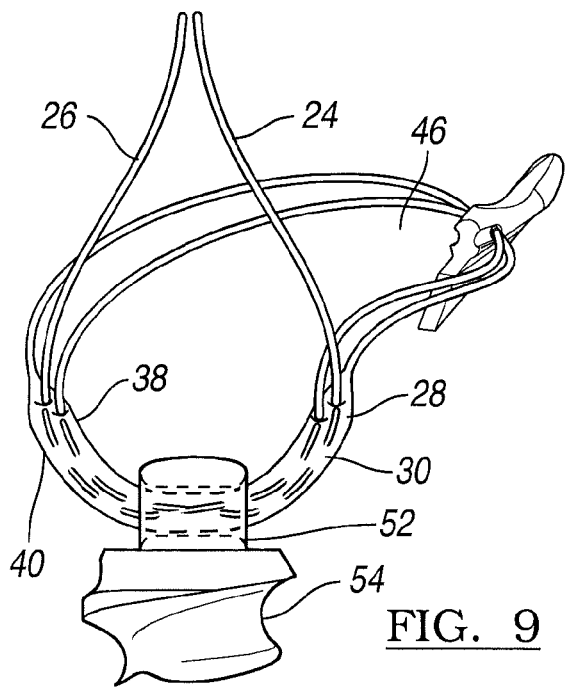
FIGS. 9-11 represent the coupling of the suture construction according to FIG. 5 to a bone screw.
Figure 10:
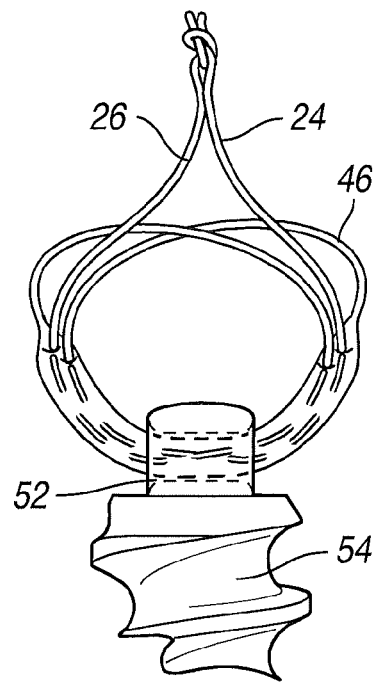

FIGS. 5-7 represent alternate constructions wherein a plurality of loops 46a-d are formed by passing the first and second ends 24 and 26 through the longitudinal passage 30 multiple times. The first and second ends 24 and 26 can be passed through multiple or single apertures defined at the ends of the longitudinal passage 30. The tensioning of the ends 24 and 26 cause relative translation of the sides of the suture with respect to each other.

Upon applying tension to the first and second ends 24 and 26 of the suture 22, the size of the loops 46a-d is reduced to a desired size or load. At this point, additional tension causes the body of the suture defining the longitudinal passage 30 to constrict about the parallel portions of the suture within the longitudinal passage 30. This constriction reduces the diameter of the longitudinal passage 30, thus forming a mechanical interface between the exterior surfaces of the first and second parallel portions as well as the interior surface of the longitudinal passage 30.

As seen in FIGS. 8-11, the suture construction can be coupled to various biocompatible hardware. In this regard, the suture construction 20 can be coupled to an aperture 52 of the bone engaging fastener 54. Additionally, it is envisioned that soft tissue or bone engaging members 56 can be fastened to one or two loops 46. After fixing the bone engaging fastener 54, the members 56 can be used to repair, for instance, a meniscal tear. The first and second ends 24, 26 are then pulled, setting the tension on the loops 46, thus pulling the meniscus into place. Additionally, upon application of tension, the longitudinal passage 30 is constricted, thus preventing the relaxation of the tension caused by relative movement of the first and second parallel portions 38, 40, within the longitudinal passage 30.

As seen in FIGS. 9-11B, the loops 46 can be used to fasten the suture construction 20 to multiple types of prosthetic devices. As described further below, the suture 22 can further be used to repair and couple soft tissues in an anatomically desired position. Further, retraction of the first and second ends allows a physician to adjust the tension on the loops between the prosthetic devices.

Figure 11A:
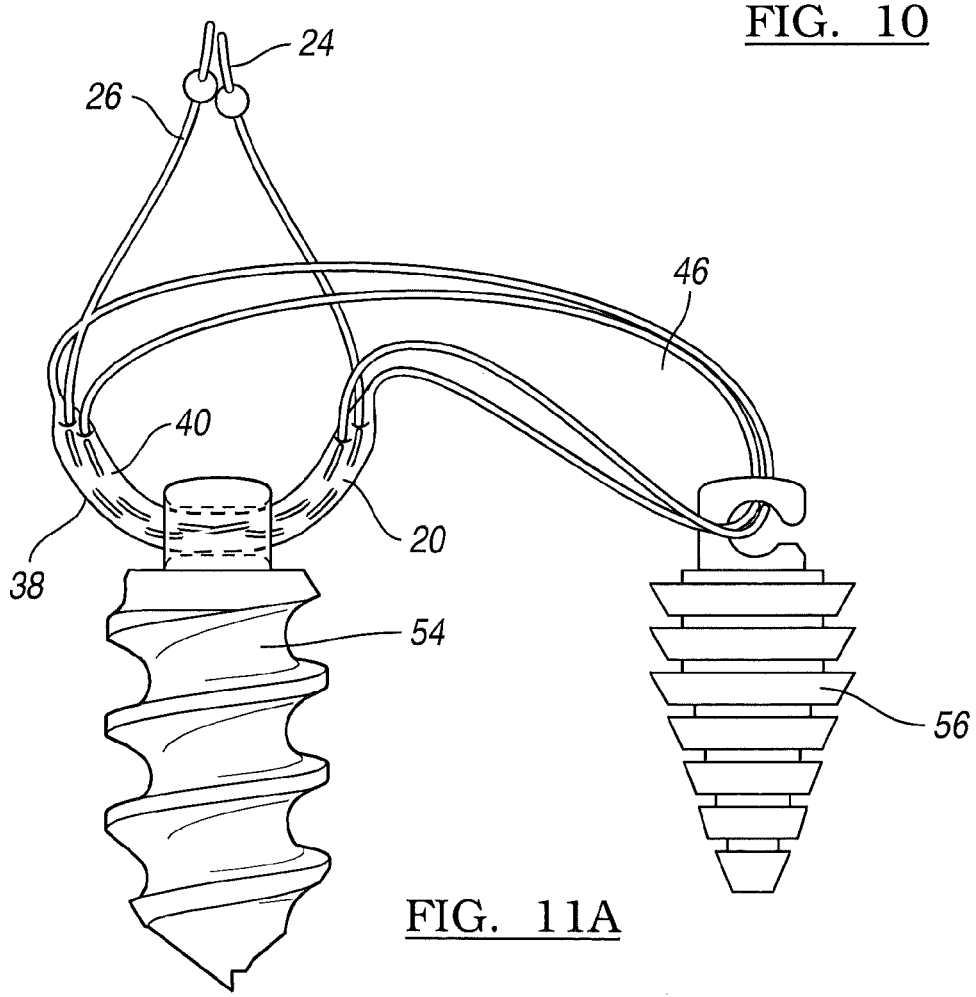
Figure 11B:
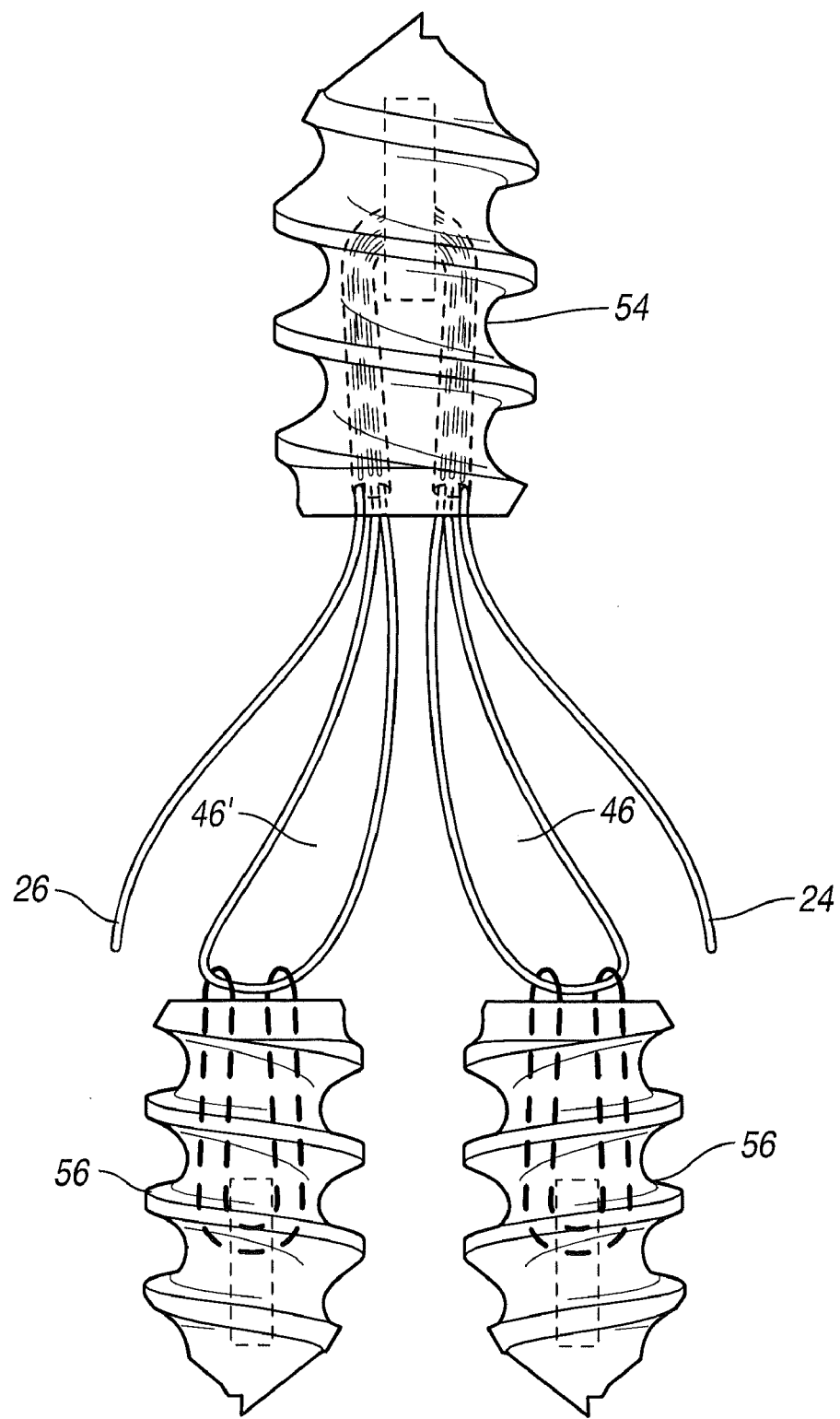

FIG. 11b represents the coupling of the suture construction according to FIG. 2B with a bone fastening member. Coupled to a pair of loops 46 and 46' are tissue fastening members 56. The application of tension to either the first or second end 24 or 26 will tighten the loops 46 or 46' separately.

Figure 12A:
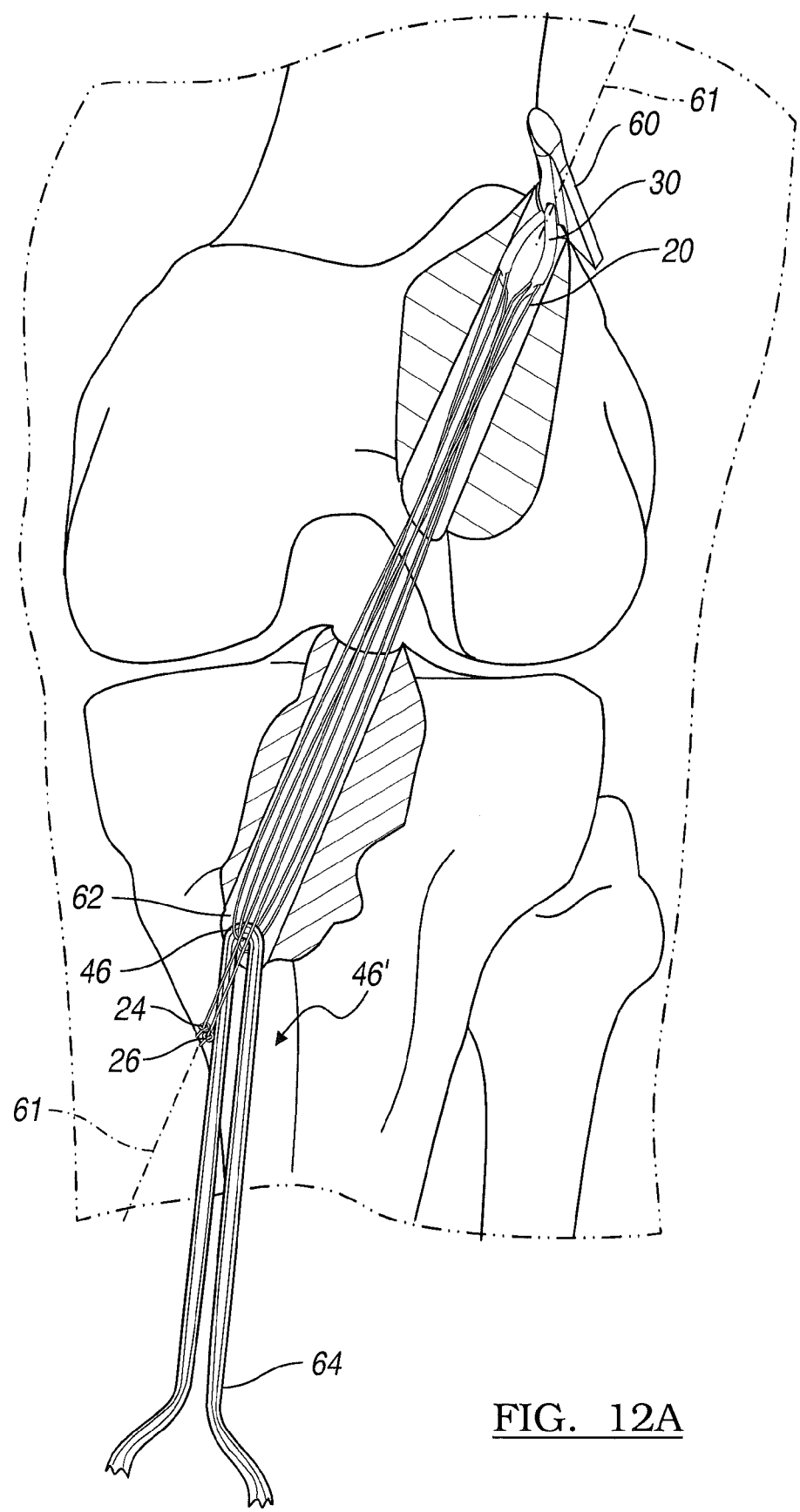
FIGS. 12A-12E represent the coupling of a soft tissue to an ACL replacement in a femoral/humeral reconstruction.
Figure 12B:
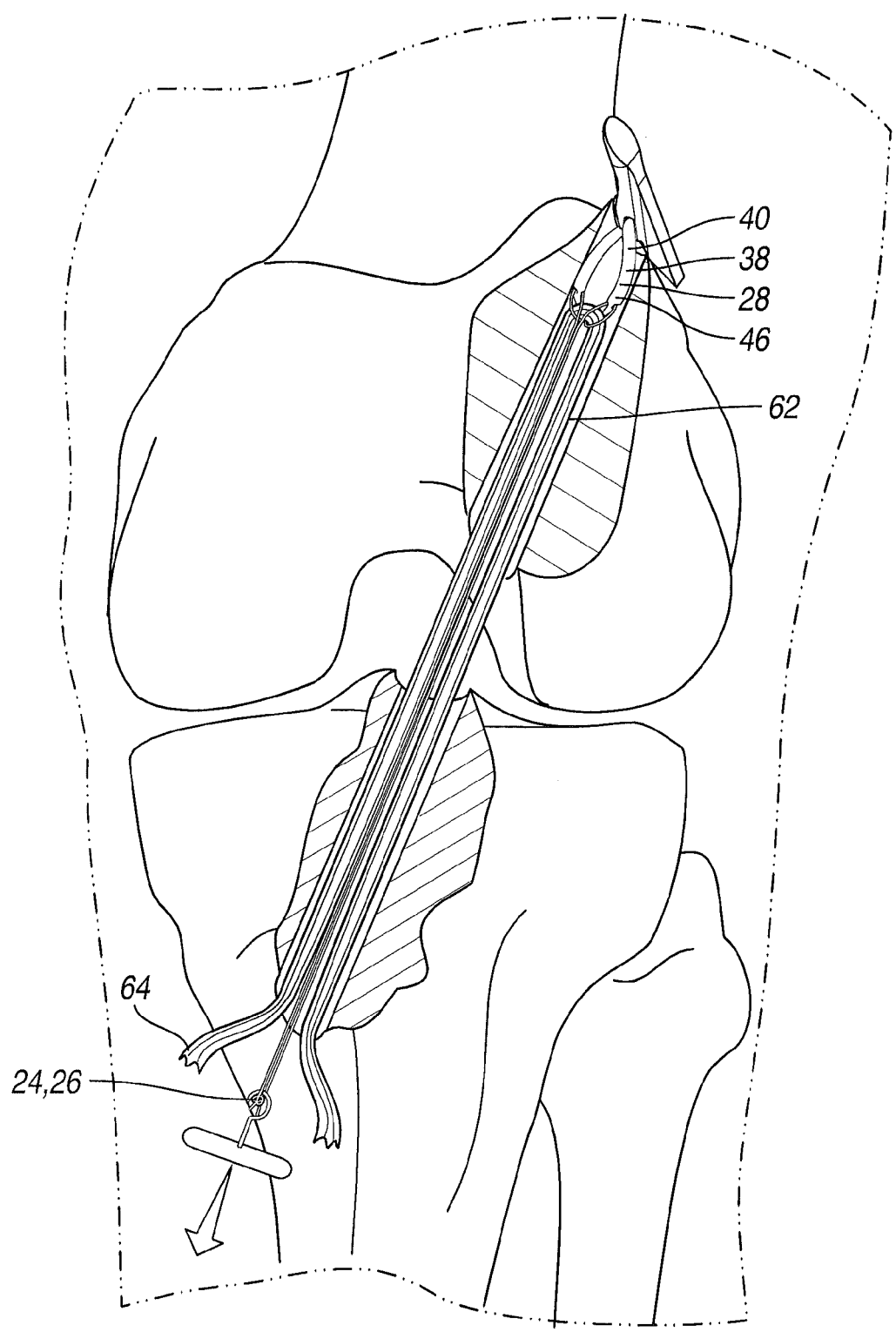

FIGS. 12A-12E represent potential uses of the suture constructions 20 in FIGS. 2A-7 in an ACL repair. As can be seen in FIG. 12A, the longitudinal passage portion 30 of suture construction 20 can be first coupled to a fixation member 60. The member 60 can have a first profile which allows insertion of the member 60 through the tunnel and a second profile which allows engagement with a positive locking surface upon rotation. The longitudinal passage portion 30 of the suture construction 20, member 60, loops 46 and ends 24, 26 can then be passed through a femoral and tibial tunnel 62. The fixation member 60 is positioned or coupled to the femur. At this point, a natural or artificial ACL 64 can be passed through a loop or loops 46 formed in the suture construction 20. Tensioning of the first and second ends 24 and 26 applies tension to the loops 46, thus pulling the ACL 64 into the tunnel. In this regard, the first and second ends are pulled through the femoral and tibial tunnel, thus constricting the loops 46 about the ACL 64 (see FIG. 12B).

As shown, the suture construction 20 allows for the application of force along an axis 61 defining the femoral tunnel. Specifically, the orientation of the suture construction 20 and, more specifically, the orientation of the longitudinal passage portion 30, the loops 46, and ends 24, 26 allow for tension to be applied to the construction 20 without applying non-seating forces to the fixation member 60. As an example, should the loops 24, 26 be positioned at the member 60, application of forces to the ends 24, 26 may reduce the seating force applied by the member 60 onto the bone.

Figure 12C:
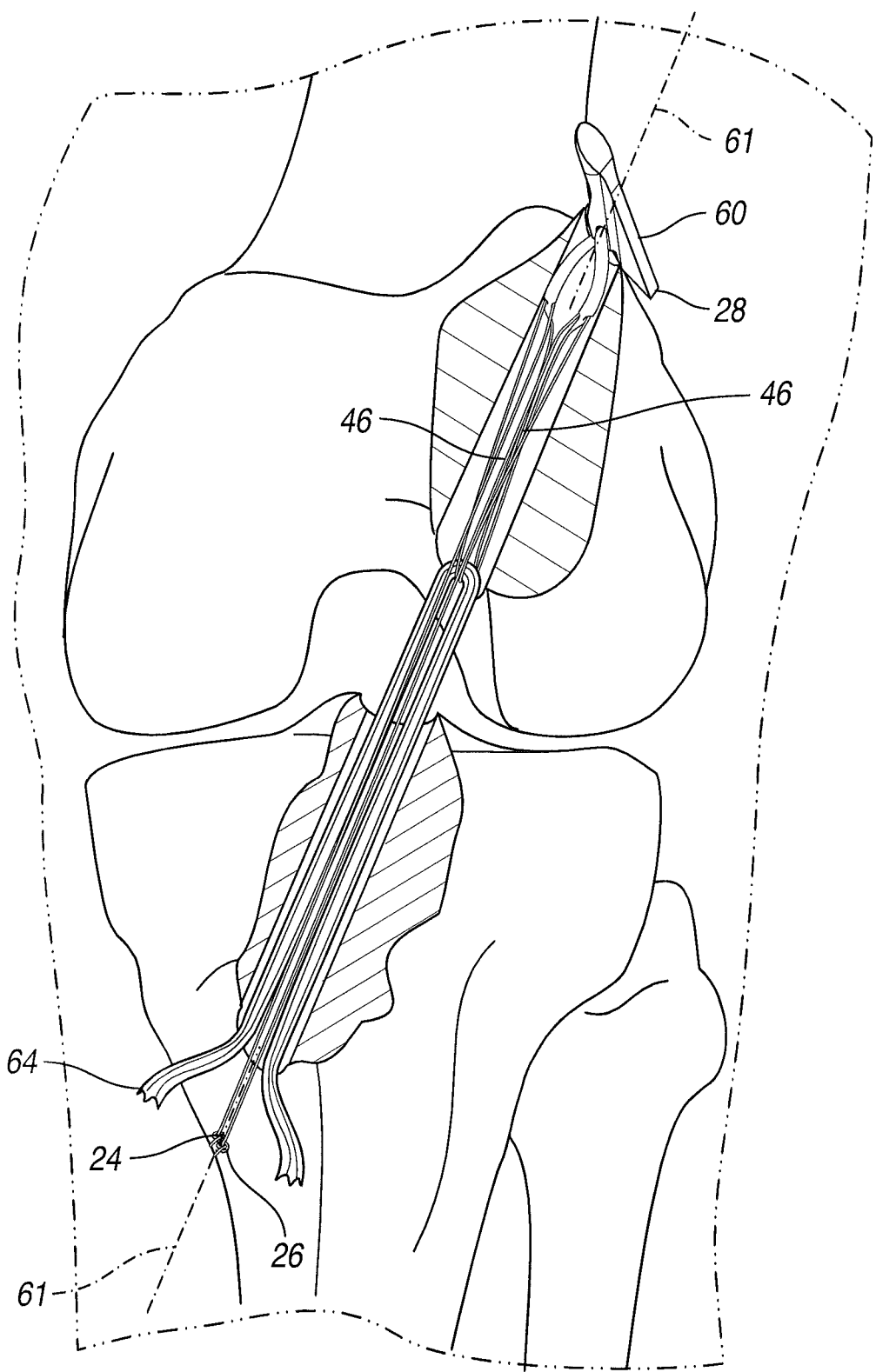
Figure 12D:
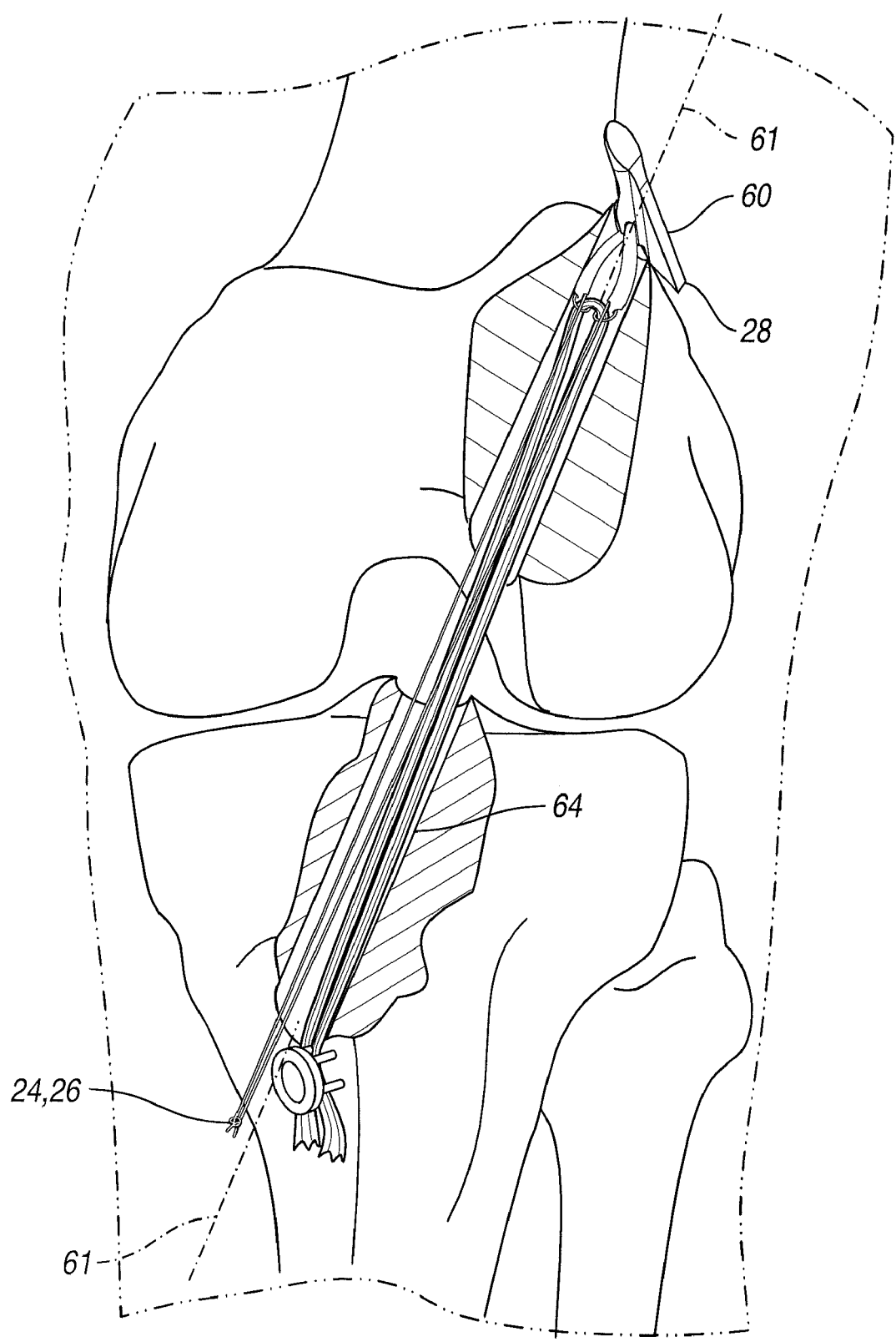

As best seen in FIG. 12C, the body portion 28 and parallel portions 38, 40 of the suture construction 20 remain disposed within to the fixation member 60. Further tension of the first ends draws the ACL 64 up through the tibial component into the femoral component. In this way, suture ends can be used to apply appropriate tension onto the ACL 64 component. The ACL 64 would be fixed to the tibial component using a plug or screw as is known.

Figure 12E:
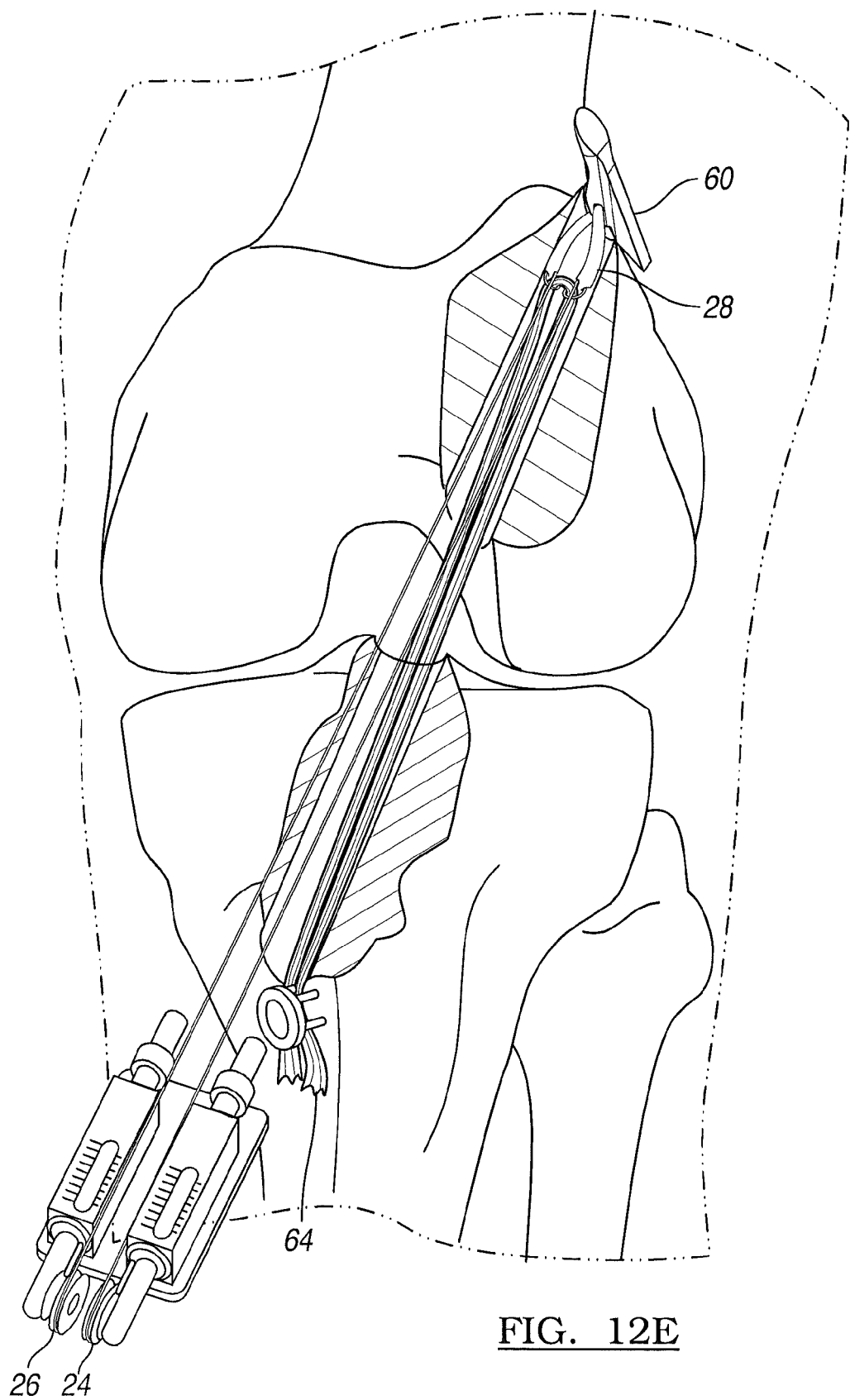
Figure 13A:
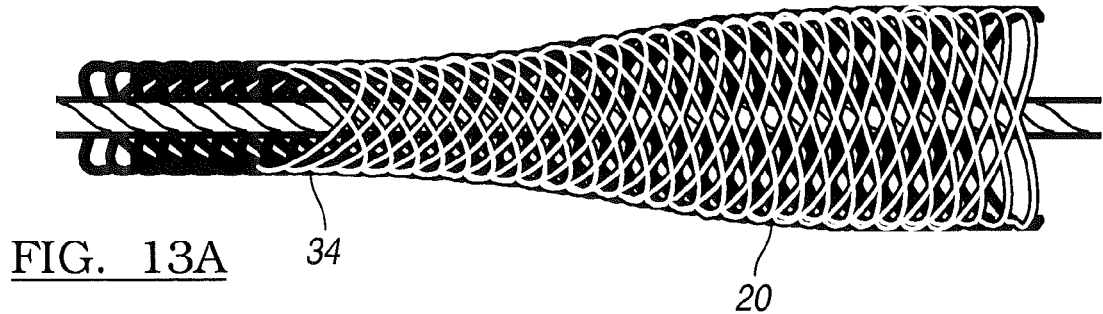
FIGS. 13A-13D represent a close-up view of the suture shown in FIGS. 1-11C.
Figure 13B:
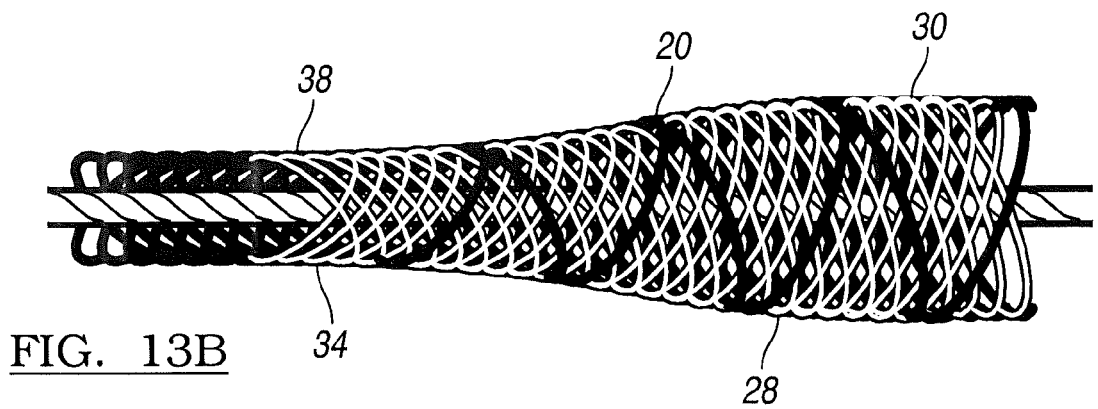
Figure 13C:
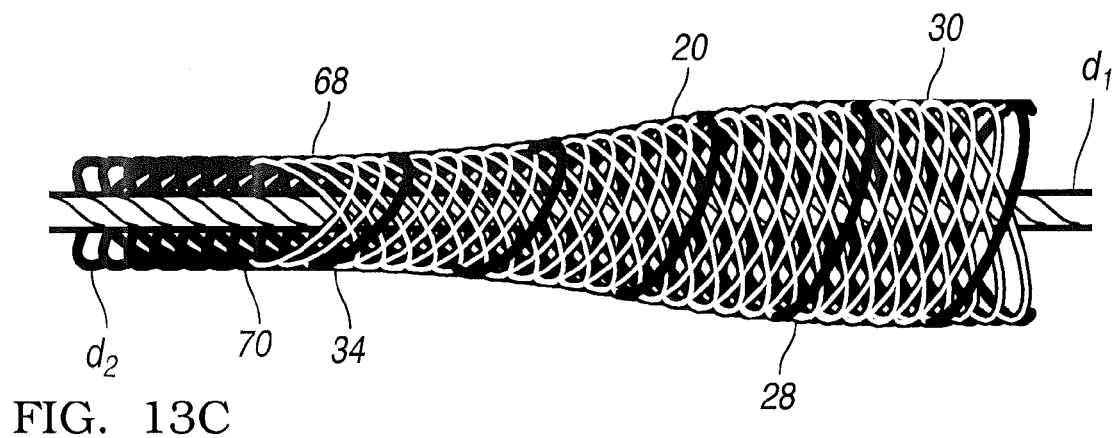
Figure 13D:
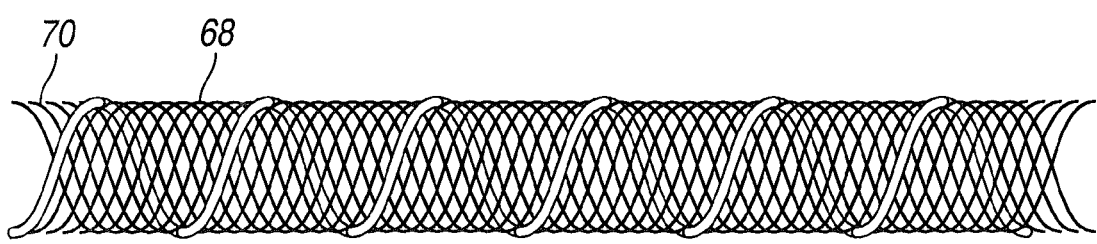

After feeding the ACL 64 through the loops 46, tensioning of the ends allows engagement of the ACL with bearing surfaces defined on the loops. The tensioning pulls the ACL 64 through a femoral and tibial tunnel. The ACL 64 could be further coupled to the femur using a transverse pin or plug. As shown in FIG. 12E, once the ACL is fastened to the tibia, further tensioning can be applied to the first and second ends 24, 26 placing a desired predetermined load on the ACL. This tension can be measured using a force gauge. This load is maintained by the suture configuration. It is equally envisioned that the fixation member 60 can be placed on the tibial component 66 and the ACL pulled into the tunnel through the femur. Further, it is envisioned that bone cement or biological materials may be inserted into the tunnel 62.

FIGS. 13A-13D represent a close-up of a portion of the suture 20. As can be seen, the portion of the suture defining the longitudinal passage 30 has a diameter $d_1$ which is larger than the diameter $d_2$ of the ends 24 and 26. The first aperture 32 is formed between a pair of fiber members. As can be seen, the apertures 32, 34 can be formed between two adjacent fiber pairs 68, 70. Further, various shapes can be braided onto a surface of the longitudinal passage 30.

The sutures are typically braided of from 8 to 16 fibers. These fibers are made of nylon or other biocompatible material. It is envisioned that the suture 22 can be formed of multiple type of biocompatible fibers having multiple coefficients of friction or size. Further, the braiding can be accomplished so that different portions of the exterior surface of the suture can have different coefficients of friction or mechanical properties. The placement of a carrier fiber having a particular surface property can be modified along the length of the suture so as to place it at varying locations within the braided constructions.

The description of the invention is merely exemplary in nature and, thus, variations that do not depart from the gist of the invention are intended to be within the scope of the invention. For example, any of the above mentioned surgical procedures is applicable to repair of other body portions. For example, the procedures can be equally applied to the repair of wrists, elbows, ankles, and meniscal repair. The suture loops can be passed through bores formed in soft or hard tissue. It is equally envisioned that the loops can be passed through or formed around an aperture or apertures formed in prosthetic devices e.g. humeral, femoral or tibial stems. Such variations are not to be regarded as a departure from the spirit and scope of the invention.

What is claimed is:

1. A method of surgically implanting a suture comprising:
   passing the suture through a bore defined by a first fastener;
   passing a first end of the suture through a first aperture defined by the suture into a passage portion defined by the suture and out a second aperture defined by the suture so as to place the first end outside of the passage portion and form a first loop; and
   passing a second end of the suture through the second aperture into the passage portion and out the first aperture so as to place the second end outside of the passage portion and form a second loop;
   positioning the passage portion within the bore;
   applying tension onto the first and second ends to constrict at least one of the first and second loops; and
   coupling the first fastener to a patient.

2. A method of surgically implanting a suture according to claim 1 further comprising:
   forming a femoral tunnel;
   threading the first and second ends and the first and second loops through the femoral tunnel;
   threading a soft tissue through the first and second loops; and
   applying tension onto the first and second ends to constrict the first and second loops about the soft tissue.

3. The method according to claim 2 further comprising injecting cement into the femoral tunnel.

4. The method according to claim 2 wherein applying tension onto the first and second ends includes drawing the soft tissue into the femoral tunnel.

5. The method according to claim 2 further comprising forming a tibial tunnel coaxial to the femoral tunnel in a tibia.

6. The method according to claim 2 comprising forming the first aperture between fibers defining the suture.

7. The method according to claim 2 comprising forming the first and second apertures between fibers defining the suture.

8. The method according to claim 2 wherein the first aperture is located between the first end and the second aperture.

9. The method according to claim 2 wherein the first aperture is located between the second end and the second aperture.

10. The method according to claim 2 further comprising passing the first end through the first aperture a second time and through the passage portion and out the second aperture a second time.

11. The method according to claim 10 further comprising passing the second end through the second aperture a second time, and further passing the second end through the passage portion and through the first aperture a second time.

12. A method of surgically implanting a suture comprising:
    passing the suture through an aperture defined by a first bone engaging member;
    passing a first end of the suture through a first aperture defined by the suture into a passage portion defined by the suture and out a second aperture defined by the suture so as to place the first end outside of the passage portion and form a first loop; and
    passing a second end of the suture through the second aperture into the passage portion and out the first aperture so as to place the second end outside of the passage portion and form a second loop;
    threading a second fastener through at least one of the first and second loops;
    applying tension one of the first and second ends to constrict at least one of the first and second loops; and
    coupling the first bone engaging member to a patient.

13. The method according to claim 12 further comprising coupling the second fastener to a bone.

14. The method according to claim 12 further comprising coupling the second fastener to a meniscus.

15. The method according to claim 12 wherein coupling the first fastener is coupling the first fastener to a bone.

16. A method of surgically implanting a suture comprising:
    forming a first tunnel in a first bone;
    providing a locking member having a first profile which allows insertion of the locking member through the first tunnel and a second profile which allows engagement with the positive locking surface upon rotation of the locking member;
    passing the suture through a bore defined in the locking member;
    passing a first end of the suture through a first aperture into a passage portion defined by the suture and out a second aperture defined by the suture so as to place the first end outside of the passage portion and define a first loop; and
    passing a second end of the suture through the second aperture into the passage portion and out the first aperture so as to place the second end outside of the passage portion, and define a second loop;
    placing the passage portion within the bore;
    threading the first and second ends and the first and second loops and the locking member through the first tunnel;
    threading the soft tissue replacement through the first and second loops so as to engage bearing surfaces on the first and second loops; and
    engaging the locking member.

17. The method according to claim 16 further including rotating the locking member.

18. The method according to claim 17 further comprising applying tension onto the first and second ends to constrict the first and second loops about the soft tissue.

19. The method according to claim 18 wherein applying tension onto the first and second ends includes drawing the soft tissue into the first tunnel.

20. The method according to claim 18 further including forming a second tunnel in a second bone; and
    threading the first and second ends and the first and second loops through the second tunnel.

21. The method according to claim 19 further comprising coupling the soft tissue to the first bone with a bone engaging fastener and applying additional tension onto the first and second ends until the soft tissue has a predetermined tension.

* * * * *

UNITED STATES PATENT AND TRADEMARK OFFICE
CERTIFICATE OF CORRECTION

| | | |
|---|---|---|
| PATENT NO. | : 7,601,165 B2 | Page 1 of 1 |
| APPLICATION NO. | : 11/541506 | |
| DATED | : October 13, 2009 | |
| INVENTOR(S) | : Kevin T. Stone | |

It is certified that error appears in the above-identified patent and that said Letters Patent is hereby corrected as shown below:

Item No. (56), References Cited, U.S. Patent Documents, page 2, col. 1, Ref. No. 50, "Coins" should be --Goins--.

Item No. (56), References Cited, Foreign Patent Documents, page 9, col. 1, Ref. No. 2, "AU8963869 2/ 1971" should be --AU 5963869 2/1971--.

Col. 2, line 55, "FIGs. "1-11C" should be --FIGs. 1-11B--.
Col. 4, line 5, "FIG. 11b" should be --FIG. 11B--.
Col. 6, line 17, after "tension" insert --to--.

Signed and Sealed this

Sixteenth Day of March, 2010

David J. Kappos
*Director of the United States Patent and Trademark Office*